(12) United States Patent
Baltzer et al.

(10) Patent No.: US 7,105,494 B1
(45) Date of Patent: Sep. 12, 2006

(54) VIRAL AND NON-VIRAL VECTORS AS VEHICLES FOR DELIVERING TRANSGENES FOR TREATING BONE PATHOLOGIES

(75) Inventors: Axel W. Baltzer, Neuss (DE); Paul D. Robbins, Mt. Lebanon, PA (US); Christopher H. Evans, Cohasset, MA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/561,524

(22) Filed: Apr. 28, 2000

Related U.S. Application Data

(63) Continuation-in-part of application No. PCT/EP98/06849, filed on Oct. 29, 1998.

(30) Foreign Application Priority Data

Oct. 29, 1997 (DE) ............................... 197 47 718
Oct. 29, 1997 (DE) ............................... 197 47 719

(51) Int. Cl.
*A61K 48/00* (2006.01)

(52) U.S. Cl. ...................... 514/44; 424/93.1; 424/93.2; 424/93.21

(58) Field of Classification Search ................ 514/44; 536/23.5, 23.51, 23.52; 435/455; 424/93.1, 424/93.2, 93.21
See application file for complete search history.

(56) References Cited

U.S. PATENT DOCUMENTS

| | | | |
|---|---|---|---|
| 5,032,407 | A | 7/1991 | Wagner et al. |
| 5,460,959 | A | 10/1995 | Mulligan et al. |
| 5,650,096 | A | 7/1997 | Harris et al. |
| 5,665,350 | A | 9/1997 | Quesenberry |
| 5,670,488 | A | 9/1997 | Gregory et al. |
| 5,674,844 | A | 10/1997 | Kuberasampath et al. |
| 5,719,131 | A | 2/1998 | Harris et al. |
| 5,750,103 | A | 5/1998 | Cherskey |
| 5,763,416 | A | 6/1998 | Bonadio et al. |
| 5,767,099 | A | 6/1998 | Harris et al. |
| 5,824,655 | A | 10/1998 | Border |
| 5,844,079 | A | 12/1998 | Ingham et al. |
| 5,858,355 | A | 1/1999 | Glorioso et al. |
| 5,910,487 | A | 6/1999 | Yew et al. |
| 5,912,239 | A | 6/1999 | Siegel et al. |
| 5,942,496 | A | 8/1999 | Bonadio et al. |
| 5,948,767 | A | 9/1999 | Scheule et al. |
| 5,948,925 | A | 9/1999 | Keynes et al. |
| 5,952,516 | A | 9/1999 | Siegel et al. |
| 5,981,275 | A | 11/1999 | Armentano et al. |
| 6,090,790 | A * | 7/2000 | Eriksson .................. 514/44 |
| 6,737,413 | B1 * | 5/2004 | Koopman et al. ............ 514/44 |

FOREIGN PATENT DOCUMENTS

| | | |
|---|---|---|
| EP | 890639 | 1/1999 |
| WO | 9118047 | 11/1991 |
| WO | 9207943 | 5/1992 |
| WO | 9514232 | 5/1995 |
| WO | 9527518 | 10/1995 |
| WO | WO 9617057 A1 * | 6/1996 |
| WO | 9623001 | 8/1996 |
| WO | 9722623 | 6/1997 |
| WO | 9806849 | 2/1998 |
| WO | 9813383 | 4/1998 |
| WO | 9921589 | 5/1999 |

OTHER PUBLICATIONS

Alden et al., "The use of bone morphogenetic protein gene therapy in craniofacial bone repair," J. Craniofacial Surg. 11(3): 167-175, Jan. 2000.*

Graham et al, "Characteristics of a human cell line transformed by DNA from Human Adenovirus", *J. Gene Virol.*, vol. 36, 1977, pp. 59-72.

Srivastava et al., "Nucleotide sequence organization of the adeno-associated virus 2 genome", *J. Virol.*, vol. 45, 1983, pp. 555-564.

Sampath et al., "Isolation of osteogenin, an extracellular matrix-associated, bone-inductive protein by heparin affinity chromatography", *Proc. Natl. Acad. Sci. USA*, vol. 84, 1987, pp. 7109-7113.

Zaslav et al., "Management of resistant pseudoarthrosis of long bones", *Clin. Orthop. Rel. Res.*, vol. 233, 1988, pp. 234-242.

Yamaguchi et al., "Recombinant human BMP-2 stimulates osteoblastic maturation and inhibits myogenic differentiation in vitro", *J. Cell. Biol.*, vol. 113, 1991, pp. 681-687.

(Continued)

*Primary Examiner*—Scott D. Priebe
(74) *Attorney, Agent, or Firm*—Joseph Hyosuk Kim; JHK Law

(57) ABSTRACT

The present invention relates to a method for treating bone pathologies comprising delivering a viral or non-viral delivery vehicle comprising genetic information (e.g. a transgene) encoding a therapeutic osteoinductive factor to target cells in vivo enabling the cells to produce the osteoinductive factor at the site of the bone pathology. The delivery is achieved by a simplified method which does not require cumbersome ex vivo techniques or additional matrix or scaffolding agents. Such viral and non-viral delivery vehicles of the present invention are derived from the following nonlimiting examples: adenoviruses, adeno-associated viruses, retroviruses, herpes simplex viruses, liposomes, and plasmids. The osteoinductive factors include, but are not limited to, growth factors, cytokines, growth factor inhibitors and cytokine inhibitors.

9 Claims, 13 Drawing Sheets

OTHER PUBLICATIONS

Hammonds et al., "Bone inducing activity of mature BMP-2b produced from a hybrid BMP-2 a/b precursor", *Mol. Endocrinol.*, vol. 5, 1991, pp. 149-155.

Gao et al., "A novel cationic lipsome reagent for efficient transfetion of mammalian cells", *Biochem. Biophys. Res. Commun.*, vol. 179, 1991, pp. 280-285.

Albertson et al., "The use of periosteally vascularized autografts to augment the fixation of large segmental allografts", *Clin. Orthop.*, vol. 269, 1991, pp. 113-119.

Yasko et al., "The healing of segmental bone defects, induced by recombinant human bone morphogenetic protein (rhBMP)", *J. Bone Joint Surg.*, vol. 74-A, 1992, pp. 659-670.

Minami et al., "Treatment of infected segmental defect of long bone with vascularized bone transfer", *J. Reconstr. Microsurg.*, vol. 8, 1992, pp. 75-82.

Aspenberg et al., "Bone morphogenetic protein induces bone in the squirrel monkey, but bone matrix does not", *Acta Orthop. Scand.*, vol. 63, 1992, pp. 619-622.

Wang et al., "Bone morphogenetic proteins (BMPs): therapeutic potential in healing bony defects", *Trends Biotechnol.*, vol. 11, 1993, pp. 379-383.

Südkamp et al., "Incidence of non-unions in open fractures: analysis of 948 open fractures", *Akt Traumatol*, vol. 23, 1993, pp. 59-67.

Sampath et al., "Drosophila TGF-β superfamily proteins induce endochrondral bone formation in mammals", *Proc. Natl. Acad. Sci. USA*, vol. 90, 1993, pp. 6004-6008.

Gerhart et al., "Healing segmental femoral defects in sheep using recombinant human one morphogenetic protein", *Clin. Ortop. Rel. Res.*, vol. 293, 1993, pp. 317-326.

Bandara et al., "Intraarticular expression of biologically active interleukin 1-receptor-antagonist protein by ex vivo gene transfer", *Proc. Natl. Acad. Sci. USA*, vol. 90, 1993, pp. 10764-10768.

Schwartz et al., "IL-1 receptor antagonist (IRAP) inhibits IL-8 production in A549 cells infected with a replication deficient recombinant adenovirus", *FASEB J.*, 1994, vol. 8, pp. 4-5.

Kimble et al., "Interleukin-1 receptor antagonist decreases bone loss and bone resorption in ovariectomized rats," *J. Clin. Invest.*, vol. 93, 1994, pp. 1959-1967.

Katagiri et al., "BMP-2 converts the differentiation pathway of C2C12 myoblasts into the osteblast lineage", *J. Cell Biol.*, vol. 6, 1994, pp. 1755-1766.

Wells et al., "The presence of an autologous marrow stromal cell layer increases glucocerebrosidase gene transduction of long term initiatine cells (LTCICs) from the bone marrow of a patient with Gaucher disease", *Gene Therapy*, vol. 2, 1995, pp. 512-520.

Evans et al., "Possible orthopedic applications of gene therapy", *J. Bone Joint Surg.*, vol. 77-A, 1995, pp. 1103-1114.

Einhorn et al., "Enhancement of fracture healing", *J. Bone Joint Surg.*, vol. 77-A, 1995, p. 940-955.

Baragi et al., "Transplantation of transduced chondrocytes protects articular cartilage from interleukin 1-induced extracellular matrix degradation", *J. Clin. Invest.*, vol. 96, 1995, pp. 2454-2460.

Wehling et al., "Neurophysiologic changes in lumbar nerve root inflammation in the rate after treatment with cytokine inhibitors", *Spine*, vol. 21, 1996, pp. 931-935.

Smith et al., "Gene delivery systems for use in gene therapy an overview of quality assurance and safety issues", *Gene Therapy*, vol. 3, 1996, pp. 190-200.

Riley et al., "Bone morphogenetic protein-1: biology and applications," *Clin. Orthop.*, vol. 324, 1996, pp. 39-46.

Mittereder et al., "Evaluation of the concentration and bioactivity of adenovirus vectors for gene therapy", *J. Virol.*, vol. 70, 1996, pp. 7498-7509.

Lind et al., "Bone morphogenetic protein-2 but not bone morphogenetic protein-4 and -6 stimulates chemotactic migration of human osteoblasts, human marrow osteoblasts, and US-OS cells", *Bone*, vol. 18, 1996, pp. 53-57.

Fang et al., "Stimulation of new bone formation by direct transfer of osteogenic plasmid genes", *Proc. Natl. Acad. Sci. USA*, vol. 93, 1996, pp. 5753-5758.

Bostrom et al., "Use of BMP-2 in the rabbit ulnar nonunion model", *Clin. Orthop. Rel. Res.*, vol. 327, 1996, pp. 272-282.

Ripamonti et al., "Recombinant transforming growth factor-β1 induces endochondral bone in the baboon and synergizes with recombinant osteogenic protein-1 (bone morphogenetic protein-7) to initiate rapid bone formation", *J. Bone Min. Res.*, vol. 12, 1997, pp. 1584-1595.

Reinecke et al., "In vitro transfer of genes in spinal tissue," *Z. Orthop. Ihre. Grenzgeb.*, vol. 135, 1997, pp. 412-416.

Pelletier et al., "In vivo suppression of early experimental osteoarthritis by interleukin-1 receptor antagonist using gene therapy", *Arthritis and Rheumatism*, vol. 40, 1997, pp. 1012-1019.

Nakaoka et al., "Inhibition of rat vascular smooth muscle proliferation in vitro and in vivo by bone morphogenetic protein-2", *J. Clin. Invest.*, vol. 100, 1997, pp. 2824-2832.

Moroni et al., "Surgical treatment of isolated forearm non-union with segmental bone loss", *Injury*, vol. 28, 1997, pp. 497-504.

Kang et al., "Gene therapy for arthritis: principles and clinical practice", *Biochem. Soc. Trans.*, vol. 25, 1997, pp. 533-537.

Balk et al., "Effect of rhBMP-2 on the osteogenic potential of bone marrow stromal cells from an osteogenesis imperfecta mouse (oim)", *Bone*, vol. 21, 1997, pp. 7-15.

Bakker et al., "Prevention of murine collagen-induced arthritis in the knee and ipsilateral paw by local expression of human interleukin-1 receptor antagonist protein in the knee", *Arthritis Rheum.*, vol. 40, 1997, pp. 893-900.

Arai et al., "Adenovirus vector-mediated gene transduction to chondrocytes: in vitro evaluation of therapeutic efficacy of tansforming growth factor-beta 1 and heat shock protein 70 gene transduction", *J. Rheumatol.*, vol. 24, 1997, pp. 1787-1795.

Riew et al., "Induction of bone formation using a recombinant adenoviral vector carrying the human BMP-2 gene in a rabbit spinal fusion model", *Calcif. Tissue Int.*, vol. 63, 1998, pp. 357-360.

Niyibizi et al., "Potential role for gene therapy in the enhancement of fracture healing", *Clin. Orthop. Rel. Res.*, vol. 355S, Oct. 1998, pp. 148-153.

Nishida et al., "Adenovirus-mediated gene transfer to nucleus pulposus cells. Implications for the treatment of intervertebral disc degeneration", *Spine*, vol. 23, 1998, pp. 2437-2442.

Mason et al., "Expression of human bone morphogenetic protein 7 in primary rabbit periosteal cells: potential utility in gene therapy for osteochondral repair", *Gene Ther.*, vol. 5, 1998, pp. 275-282.

Liu et al., Intraspinal grafting of fibroblasts genetically modified by recombinant adenoviruses, *Neuroreport*, vol. 9, 1998, pp. 1075-1079.

Lieberman et al., "Regional gene therapy with a BMP-2 producing murine stromal cell line induces heterotopic and orthotopic bone formation in rodents", *J. Orthop. Res.*, vol. 16, 1998, pp. 330-339.

Lee et al., "Phenotype, function and in vivo migration and survival of allogeneic dendritic cell progenitors genetically engineered to express TGF-beta", *Transplantation*, vol. 66, 1998, pp. 1810-1817.

Lattanzi et al., "High efficiency myogenic conversion of human fibroblasts by adenoviral vector-mediated MyoD gene transfer. An alternative strategy for ex vivo gene therapy of primary myopathies," *J. Clin. Invest.* vol. 101, 1998, pp. 2119-2128.

Kishi et al., "Bone responses at various skeleral sites to human parathyroid hormone inovarectomized rats: effects of long-term administration, withdrawal and readministration", *Bone*, vol. 22, 1998, pp. 515-522.

Goldstein et al., "Potential role for direct gene transfer in the augmentation of fracture healing", *Clin. Orthop. Rel. Res.*, vol. 355S, 1998, pp. 154-162.

Doherty et al., "Resurfacing of articular cartilage explants with genetically-modified human chondrocytes in vitro", *Osteoarthritis Cartilage*, vol. 6, 1998, pp. 153-159.

Chen et al., "Ex vivo fibroblast transduction in rabbits results in long-term (>600 days) factor IX expression in a small percentage of animals", *Hum. Gen. Ther.*, vol. 9, 1998, pp. 2341-2351.

Boden et al., "Lumbar spinal fusion by local gene therapy with a cDNA encoding a novel osteoinductive protein (LMP-1)", *Spine*, vol. 23, 1998, pp. 2486-1492.

Baltzer et al., "Multiple gene transfer in the rabbit femoral segmental defect model", Abstract 999, Orthopaedic Research Society, 44th Annual Meeting, Mar. 16-19, 1998, New Orleans, LA.

Baltzer, "Gene Therapy in disorders of bone healing—an experimental model", *Z. Orthop. Ihre. Grenzgeb.*, vol. 136(5), 1998, pp. Oa17.

Oyama et al., "Retrovirally transduced bone marrow stromal cells isolated from a mouse model of human osteogenesis imperfecta (oim) persist in bone and retain the ability to form cartilage and bone after extended passaging", *Gene Ther.*, vol. 6, 1999, pp. 321-329.

Nishioka et al., "Induction of systemic and therapeutic antitumor immunity using intratumoral injection of dendritic cells genetically modified to express interleukin 12", *Cancer Res.*, vol. 59, 1999, pp. 4035-4041.

Musgrave et al., "Adenovirus-mediated direct gene therapy with bone morphogenetic protein-2 produces bone", *Bone*, vol. 24, 1999, pp. 541-547.

Lieberman et al., "The effect of regional gene therapy with bone morphogenetic protein-2 producing bone-marrow cells on the repair of segmental femoral defects in rats", *J. Bone Joint Surg.*, vol. 81A, 1999, pp. 905-917.

Iwamoto et al., "Actions of hedgehog proteins on skeletal cells", *Crit. Rev. Oral Bio. Med.*, vol. 10, 1999, pp. 477-486.

Greenfield ed., "Manufactured protein designed to promote bone growth shows 'excellent' results", *Clinica*, vol. 846, 1999, p. 13.

Francheschi, "The developmental control of osteoblast-specific gene expression: role of specific transcription factors and the extracellular matrix environment", *Crit. Rev. Oral. Bio. Med.*, vol. 10, 1999, pp. 40-57.

Evans et al., "Expression of chimeric granulocyte-macrophage colony-stimulating factor/interleukin 2 receptors in human cytotoxic T lymphocyte clones results in granulocyte-macrophage colony-stimulating factor-dependent growth", *Hum. Gene Ther.*, vol. 10, 1999, pp. 1941-1951.

Bonadio et al., "Localized direct plasmid gene delivery in vivo: prolonged therapy results in reproducible tissue regeneration", *Nature Med.*, vol. 5, 1999, pp. 753-759.

Baltzer et al., "In vitro transduktion humaner osteoblastärer zellpopulationen mit retroviralen vektoren", *Z. Rheumatol.*, vol. 58, 1999, pp. 88-94.

Baltzer et al., "A gene therapy approach to accelerating bone healing: Evaluation of gene expression in a New Zealand white rabbit model", *Knee Surg. Sports Traumatol. Arthrosc.*, vol. 7, 1999, pp. 197-202.

Alden et al, "In vivo endochondral bone formation using a bone morphogenetic protein 2 adenoviral vector", Human *Gene Therapy*, vol. 10, 1999, pp. 2245-2253.

Baltzer et al., "Adenoviral based gene therapy with BMP-2 and TGF-β1 in a rabbit segmental defect model", Congress of the Orthopedic Research Society, Mar. 12-15, 2000 in Orlando, Florida, 308.

Baltzer et al., 2000, "Genetic enhancement of fracture repair: healing of an experimental segmental defect by adenoviral transfer of the BMP-2 gene", *Gene Therapy* vol. 7, 2000, pp. 734-739.

* cited by examiner

A B C

VIRAL AND NON-VIRAL VECTORS AS VEHICLES FOR DELIVERING TRANSGENES FOR TREATING BONE PATHOLOGIES

This application is a continuation-in-part of PCT/EP98/06849 of Baltzer et al. filed Oct. 29, 1998, now WO 99/21589.

INTRODUCTION

The present invention relates to the use of viral and non-viral delivery vehicles for the delivery of genetic information to target cells which enable the cells to produce biologically active proteins that are useful for the correction of bone pathologies. Such viral and non-viral delivery vehicles are derived from the following nonlimiting examples: adenoviruses, adeno-associated viruses, retroviruses, herpes simplex viruses, liposomes, and plasmids.

BACKGROUND OF INVENTION

Bone is an active tissue, continually undergoing turnover, where there are interactive cycles of bone formation and resorption. Bone resorption is generally rapid and is mediated by osteoclast cells. Resorption is followed by the appearance of osteoblast cells which form bone slowly and act to replace the resorbed tissue. Factors which control bone turnover mediated by osteoclasts and osteoblasts include systemic factors (e.g. hormones, lymphokines, growth factors, vitamins) and local factors (e.g. cytokines, adhesion molecules, lymphokines, growth factors, cytokine inhibitors). These factors, as well as others, tightly control bone turnover and their inactivation may lead to defects in bone formation and turnover.

There are a number of bone disorders associated with defects in the bone turnover cycle. These include osteoporosis, osteoplasia, bone mass loss (osteopenia), Paget's disease, etc. In addition, defects in the bone turnover/repair system can also lead to complications in clinical orthopaedics, for example, fibrous non-union following bone fracture, implant interface failures and large allograft failures. Massive bony defects often occur following trauma involving bone injuries, particularly where the injury is associated with a sudden impact, such as those occurring in motor vehicle and sports accidents. A segmental defect fracture generally ends up in a non-union if it is not treated by extended and complicated surgical procedures.

Conventional bone grafting is currently considered to be the method of choice for the treatment of segmental defect fractures, although the procedure is often unsuccessful. See Albertson et al., *Clin. Orthop.* 269:113–119 (1991); Zaslav and Meinhard, *Clin. Orthop. Rel. Res.* 233:234–242 (1988). In addition, bone grafting is often associated with a number of complications, including infections, paresthesias and pain at the grafting site. See Bestrom et al., *Clin. Orthop. Rel. Res.* 327:272–282 (1996).

Alternative techniques, such as free vascularized fibular grafting, or the use of external fixator techniques have been used to improve the surgical success rate. See Minami et al, *J. Recontr. Microsurg.* 8:75–82 (1992). A vascularized fibular graft may be superior to a conventional bone graft, but it is technically difficult and occasionally impossible to accomplish. Unsatisfactory results after surgical treatment of posttraumatic segmental bone defects are described in up to 30% of cases. See Moroni et al, *Injury* 28:497–504 (1997); Südkamp et al, *Akt Traumatol.* 23:59–67 (1993).

Segmental defects after tumor surgery are even more challenging to surgeons. The area of bone resection is generally large, all osteoconductive and osteoinductive material has been completely removed, and often the only reasonable therapy is an amputation of an extremity because of the complete lack of bony substance.

More commonly, general bone fractures are treated by casting, allowing natural mechanisms to effect wound repair. The treatment of segmental defects and less traumatic bone fractures would be benefitted by new techniques and therapies designed to stimulate the bone regeneration processes and strengthen the fracture repair process.

The patient population suffering from diseases involving loss of bone mass, such as osteoporosis, would also benefit from new techniques and therapies designed to stimulate bone regeneration processes. Osteoporosis is segregated into type Is and type II. Type Is osteoporosis occurs predominantly in middle aged women and is associated with estrogen loss at menopause, while type II osteoporosis is associated with a general advancement of age in both women and men.

An estimated 20–25 million people are at an increased risk of bone fractures due to the loss of bone mass that occurs in osteoporosis. Currently, the major focus for the treatment of osteoporosis is fracture prevention rather than fracture repair. Fractures in the elderly often do not repair quickly and are responsible for morbidity. Therefore, it would be useful to have a treatment for subjects suffering from osteoporosis which focuses on the repair of fractures. In addition, sites of low bone mass in a subject could also be treated prior to a fracture occurring with bone regeneration therapy.

Different osteoinductive and osteoconductive methods are currently under investigation for developing adequate alternatives to bone grafting. One attractive approach makes use of powerful osteogenic properties of certain growth factors. Members of the transforming growth factor β family of growth factors, including the bone morphogenic proteins (such as BMP-2, BMP-4 and BMP-7), have diverse effects on the growth and differentiation of mesenchymal cells, as well as on their ability to synthesize matrix. See Gerhart, et al., *Clin. Ortpo. Rel. Res.* 293:3170326 (1993); Ripamonti et al., *J. Bone Min. Res.* 12:1584–1595 (1997); Yasko et al., *J. Bone Joint Surg.* 74-A:659–670 (1992). An interesting feature of some of these growth factors is their osteoinductivity, the competence to induce bone formation. This has been demonstrated in vivo by the ability of purified recombinant osteoinductive proteins to induce bone formation at heterotropic sites and in different bone defect models. See Lieberman et al., *J. Orthop. Res.* 16:330–339 (1998) (bone marrow cell line infected with an adenovirus expressing recombinant BMP-2 secreted biologically active BMP-2 and effected heterotropic bone formation in quadricep muscles of immune deficient mice when transplanted thereto); Ripamonti et al., *J. Bone Min. Res.* 12:1584–1595 (1997) (induction of bone formation shown by the administration of purified recombinant TGFβ1); Sampath et al., *Proc. Natl. Acad. Sci. USA* 84:7109–7113 (1993) (induction of bone formation shown by the administration of recombinant drosophila proteins homologous to TGFβ).

In addition, the hedgehog family of proteins, described in U.S. Pat. No. 5,844,079, incorporated herein by reference, are also involved in bone formation. Members of the hedgehog gene family were initially characterized as patterning factors in embryonic development but have recently been shown to regulate skeletal formation in vertebrates. Sonic hedgehog, a member of the hedgehog family, regulates the localized production of bone morphogenic proteins and related molecules which initiate chondrocyte and osteoblast-specific differentiation. See *Crit. Rev. Oral Bio. Med.* 10:40–57 (1999). The amino-terminal fragment of Sonic hedgehog has the ability to induce ectopic cartilage and bone formation in vivo. In addition, ectopic expression of Indian hedgehog induces expression of the parathyroid hormone-related peptide, which together regulate the rate of chondrocyte maturation. Both Indian hedgehog and Sonic hedgehog stimulate osteoblast differentiation. In conclusion, members of the hedgehog family of proteins are osteoinductive proteins which are significantly involved in skeletal formation through multiple actions on chondrogenic mesenchymal cells, chondrocytes, and osteogenic cells. See *Crit. Rev. Oral. Biol. Med.* 10:477–486 (1999).

The clinical application of such osteoinductive factors may be limited by their short half-lives if administered as purified recombinant proteins to a subject. Gene transfer may be useful in overcoming this problem. The delivery of genes encoding growth factors can provide high, sustained concentrations of these factors locally and for extended periods of time. See Evans and Robbins, *J. Bone Joint Surg.* 77A:1103–1114 (1995). Moreover, endogenously synthesized proteins, in contrast to exogenously administered recombinant proteins, may have greater physiological effectiveness. See Niyibizi et al., *Clin. Orthop. Rel. Res.* 355S: 148–153 (1998).

Lieberman et al., *J. Orthop. Res.* 16:330–339 (1998) have used adenoviral vectors comprising a DNA encoding BMP-2 to accelerate healing of a segmental defect. Healing was achieved by cumbersomely delivering the adenoviral vector ex vivo to a murine stromal cell line which was then introduced in vivo by xenografting which had to be performed in an immunocompromised animal. Clinical application of such an ex vivo approach is burdened with complications. Furthermore, the efficacy of such an approach has yet to be demonstrated in an immunocompetent animal using primary cell cultures.

Both U.S. Pat. No. 5,763,416 of Bonadio et al. (the "'416" patent) and U.S. Pat. No. 5,942,496 of Bonadio et al. (the "'496" patent) disclose methods for transferring nucleic acids encoding osteoinductive agents into bone cells in situ and for stimulating bone progenitor cells for the treatment of bone-related diseases and defects. The '416 and '496 patents are limited to a method for transferring a nucleic acid encoding an osteoinductive agent wherein the nucleic acid is part of a composition comprising a structural bone-compatible matrix. Appropriate matrices of the '416 and '496 patents are described as being able to both deliver the gene composition (nucleic acid) and also provide a surface for new bone growth, i.e., the matrix should act as an in situ scaffolding through which progenitor cells may migrate.

Therefore, an improved method for the delivery of a DNA encoding an osteoinductive agent to the site of bone disease or defect which does not require ex vivo transfection/infection followed by xenografting or in vivo co-administration of a bone-compatible matrix is desired.

SUMMARY OF THE INVENTION

The object of the present invention is to provide a method of delivering a nucleic acid molecule encoding an osteoinductive factor for the treatment of bone pathologies. The delivery of the DNA is made possible by the delivery vehicles of the present invention.

Thus, the invention relates to the use of delivery vehicles such as viral and non-viral vectors. Nonlimiting examples of viral and nonviral vectors include those derived from adenoviruses, adeno-associated viruses, retroviruses, herpes simplex viruses, liposomes and plasmids, for the delivery of genetic information (e.g. DNA, RNA, protein, etc.) to mammalian cells for the treatment of bone pathologies.

DETAILED DESCRIPTION

Figure 1:
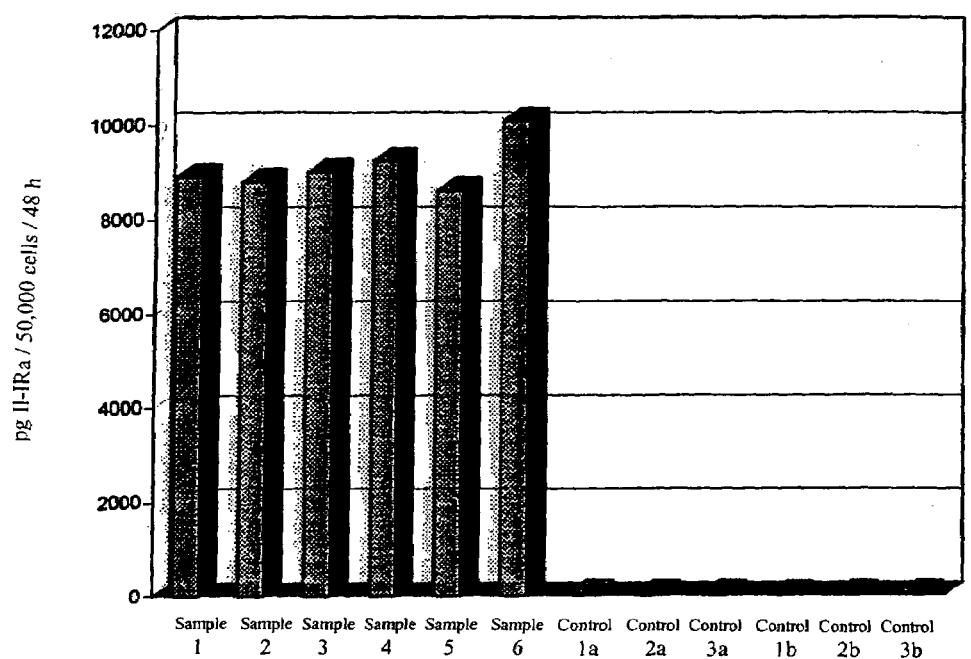
FIG. 1 is a plot showing the production of IL-1Ra from 50,000 osteoblastic cells transduced with MFG after 48 h (Samples 1–6, (values averaging 9111.5 picograms (pg)) compared with non-transduced osteoblastic cells (controls 1a–3a, values around 0 pg) and retroviral LacZ-producing transduced osteoblastic cells (controls 1b–3b, values around 0 pg). Measurements were obtained by ELISA analysis.
Figure 2:
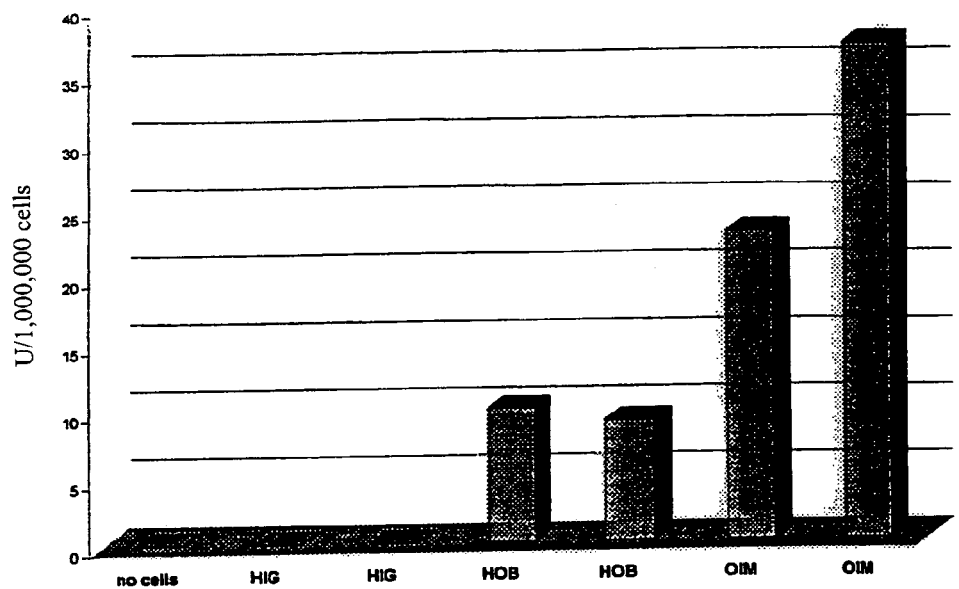
FIG. 2 is a plot of the spontaneous production of alkaline phosphatase (ALP) by human osteoblastic cells (HOB) (9.5 units per 1,000,000 cells), as well as positive controls which were carried out with murine osteogenesis imperfecta stem cells (OIM) after stimulation with BMP-2 (30 units per 1,000,000 cells). The negative controls with immortalized synovial fibroblasts (HIG-82) produce no alkaline phosphatase. Nor is any ALP present in the acellular nutritive medium (=no cells).

According to one embodiment of the present invention the delivery vehicle is an adenoviral vector. Adenoviruses are simple DNA viruses composed of double-stranded DNA and proteins. There are numerous adenovirus types some of which are pathogenic to humans, causing infections of the eyes and respiratory tract. Many adenovirus types induce tumors in experimental animals which do not correspond to the natural host, or transform cells in vitro. Adenoviral vectors are altered adenoviruses that have lost the ability for in vivo replication as well as their typical pathogenicity. See, e.g., U.S. Pat. No. 5,670,488, incorporated herein by reference.

Over 40 currently known human adenovirus types, such as, e.g. Ad2 and Ad5, are suitable for engineering a vector that can be used according to the present invention. Such adenoviral vectors are unable to replicate in vivo or in vitro in the absence of helper virus and are apathogenic due to the elimination of the essential E1 sequence. Elimination of the E1 sequence and the nonessential E3 sequence in adenoviral vectors allows for the introduction of a larger heterologous DNA insert encoding a therapeutic protein or a marker protein than would be possible if these sequences were not eliminated. After infection of a cell with an adenoviral vector, the DNA insert is episomally stored in the nucleus of the cell wherein the transcriptional and translational machinery of the cell produces the product of the DNA.

According to another embodiment of the present invention the delivery vehicle is an adeno-associated viral vector which is derived from adeno-associated viruses. An example of an adeno-associated wild-type virus is described in the *Journal of Virology*, 45:555–564 (1983), incorporated herein by reference, particularly in FIGS. 1 to 4 and also in the "Materials and Methods" and "Results" sections, to which express reference is made. The adeno-associated virus has been used for delivering a transgene to cells which expresses a marker gene for the purpose of labeling cells, as described in detail in WO 95/14232.

The delivery vehicles of the present invention may also be derived from wild-type retroviruses. Retroviruses, which are Class 6 RNA viruses, contain single-stranded ribonucleic acid (RNA) and the enzyme reverse transcriptase. By means of this enzyme the viral RNA reaching the host cell is converted into DNA, which then is integrated into the host genome. Once integrated into the host genome, the integrated retroviral DNA, called a provirus, is replicated along with the host cell genome. Retroviruses have been engineered to create retroviral vectors for use in gene technology which are replication-deficient and apathogenic. See, e.g., PCT Publication WO 92/07943, incorporated herein by reference.

Recombinant retroviral vectors, which are currently being used in human gene therapy experiments, all originate from the wild-type Moloney murine leukemia (MoMuLV) retrovirus. The recombinant retroviral vectors are structurally similar to the wild-type retrovirus, but carry a DNA insert encoding, for example, a therapeutic protein or marker protein. The recombinant retroviral vectors, according to the present invention, are replication deficient in vivo and in vitro, but are still infectious and integrate their genome into the DNA of target cells. The pathogenic retroviral genes are preferredly completely eliminated from the retroviral vectors of the present invention.

According to another aspect of the present invention, the delivery vehicles are herpes simplex virus-derived vectors. Herpes simplex viruses are neurotropic human DNA containing viruses which can, as wild-type viruses, cause a latent-type infection in neurons. The herpes simplex virus can be engineered to produce a herpes simplex viral vector that is replication-deficient and apathogenic. A particular advantage of the herpes simplex virus-derived vectors is that they are capable of carrying large DNA inserts.

In addition, the delivery vehicles of the present invention can be nonviral liposomal vectors which can contain a transgene encoding a growth factor, cytokine or a cytokine or growth factor inhibitor, and can be used to transfect mammalian cells. With regard to liposomal vectors, reference is made to the publication of Gao and Huang, *Biochem. Biophys. Res. Commun.* 179: 280–285 (1991), incorporated herein by reference. Cationic amphiphiles can also be used to make the nonviral liposomal vectors of the present invention. With respect to cationic amphiphiles, reference is made to U.S. Pat. Nos. 5,650,096; 5,719,131; 5,767,099; 5,910,487; 5,912,239; 5,948,767; 5,948,925 and 5,952,516, incorporated herein by reference.

Other non-viral delivery vehicles of the present invention include plasmids which can contain a transgene encoding a growth factor, cytokine, growth factor inhibitor or a cytokine inhibitor, and can be used to transfect mammalian cells. With regard to plasmids used as vectors, reference is made to the publication of Smith et al., *Gene Therapy* 3:190–200 (1996), incorporated herein by reference and U.S. Pat. No. 5,981,275, incorporated herein by reference.

The viral and non-viral delivery vehicles of the present invention can be made using techniques well known to those skilled in the art. Such techniques are readily available in, for example, Sambrook, Fritsch and Maniatis, *Molecule Cloning: A Laboratory Manual*, Third Edition (1994); Ausubel et al., *Current Protocols in Molecular Biology* (1992); Miller and Calos (editors), *Gene Transfer Vectors for Mammalian Cells* (1987); Kriegler, *Gene Transfer and Expression: A Laboratory Manual* (1991), all incorporated herein by reference.

The transgene, may be operatively linked to expression control sequences in order to optimize expression of the gene product. Expression control sequences include, but are not limited to, inducible and non-inducible promoters, enhancers, operators and other elements known to those skilled in the art. For example, the transgene may be placed under the control of a constitutive promoter or under an inducible promoter. Any promoter known in the art that is suitable for the expression of the transgene may be used with the delivery vehicles of the present invention. Expression control sequences may include, but are not limited to, the cytomegalovirus (hCMV) immediate early gene, the early or late promoters of SV40 adenovirus, the lac system, the trp system, the TAC system, the TRC system, the major operator and promoter regions of phage A, the control regions of fd, coat protein, the promoter for 3-phosphoglycerate kinase, the promoters of acid phosphatase, and the promoters of the yeast α-mating factors. Additional promoters include, inter alia, the Gal4 promoter, the ADH promoter, PGK promoter, alkaline phosphatase promoter, β-lactamase promoter and mammalian tissue specific promoters.

Transgenes are defined herein as nucleic acid molecules or structural genes that encode a particular polypeptide or protein or a ribozyme or an antisense RNA or the like. Transgenes encoding polypeptides or proteins include transgenes encoding osteoinductive factors, such as, but not limited to, growth hormones, cytokines, growth hormone inhibitors and cytokine inhibitors. Nonlimiting, specific examples of such osteoinductive factors include transforming growth factor-β (TGF-β), e.g. TGF-β 1–5; bone morphogenetic proteins (BMP), e.g. BMP-2–7; osteogenic protein-1 (OP-1), e.g. OP-1; insulin-like growth factor (IGF), e.g. IGF-1 and IGF-2; fibroblast growth factor (FGF), e.g. FGF-1 and FGF-2; platelet-derived growth factor (PDGF); inhibitors of tumor necrosis factors (TNF) e.g. TNF-β or TNF-α; interleukin-6 inhibitors, macrophage colony-stimulating factor (M-CSF) inhibitors, granulocyte/macrophage colony stimulating factor (GM-CSF) inhibitors, interleukins such as interleukin-4, interleukin-10, and interleukin-13; and the hedgehog family of proteins, e.g. Sonic hedgehog and Indian hedgehog.

By way of example, in order to insert the transgene into the vector, the transgene and vector can be contacted, under suitable conditions, with a restriction enzyme to create complementary ends on each molecule that can pair with each other and be joined together with a ligase. Alternatively, synthetic nucleic acid linkers can be ligated to the termini of the restricted transgene. These synthetic linkers contain nucleic acid sequences that correspond to a particular restriction site in the vector nucleic acid. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

In the process described according to the invention, the vectors or vehicles are used to deliver a DNA encoding therapeutic growth hormones, cytokines or cytokine inhibitors to a mammalian cell. Nonlimiting examples of such growth hormones, cytokines and cytokine inhibitors include transforming growth factor-β (TGF-β), e.g. TGF-β 1–5; bone morphogenetic proteins (BMP), e.g. BMP-2–7; osteogenic protein-1 (OP-1), e.g. OP-1; insulin-like growth factor (IGF), e.g. IGF-1 and IGF-2; fibroblast growth factor (FGF), e.g. FGF-1 and FGF-2; platelet-derived growth factor (PDGF); inhibitors of tumor necrosis factors (TNF) e.g. TNF-β or TNF-α; interleukin-6 inhibitors, macrophage colony-stimulating factor (M-CSF) inhibitors, granulocyte/macrophage colony stimulating factor (GM-CSF) inhibitors, interleukins such as interleukin-4, interleukin-10 and interleukin-13; and the hedgehog family of proteins, e.g. Sonic hedgehog and Indian hedgehog.

According to a particular embodiment of the present invention, mammalian cells are animal or human cells. In a preferred embodiment of the present invention, the mammalian cells are bone cells, bone marrow cells, connective tissue cells or muscle cells.

The delivery vehicles of the present invention may be administered to a cell or subject by any technique known in the art including transfection and infection. Routes of administration to a subject include, but are not limited to, parenteral routes, intraosseous routes, local administration at the site of the bone pathology, direct delivery to target cells, organs or tissues, intranasal routes, intravenous routes, intramuscular routes, subcutaneous routes, intradermal routes and oral routes of administration. The delivery vehicles of the present invention may also be administered via inhalation of liquid or dry powder aerosols. In one aspect of the invention, the delivery vehicle is administered via a parenteral route or an intraosseous route. In a preferred embodiment of the invention, the delivery vehicle is administered locally at the site of a bone pathology.

Dosage of the delivery vehicle which is to be administered to an subject is determined with reference to various parameters, including the condition to be treated, the age, weight and clinical status of the subject and the particular molecular defect of the bone pathology requiring the provision of a therapeutic protein. The dosage is preferably chosen so that administration causes a specific phenotypic result, and particularly the healing of bone. Dosages of the delivery vehicle of the present invention which can be used for example in providing a therapeutic transgene contained in a vector to a subject for persistent expression of a biologically active therapeutic osteoinductive factor encoded by the transgene and to achieve bone formation range, for example, for adenoviral vectors, from approximately $10^8$ infectious units (I.U.) to $10^{11}$ I.U. for humans. The range may be higher for adeno-associated viral vectors and may be lower for herpes simplex viral vectors.

It is especially advantageous to formulate compositions in dosage unit form for ease of administration and uniformity of dosage. "Dosage unit form" as used herein refers to physically discrete units suited as unitary dosages for the subjects to be treated, each unit containing a predetermined quantity of active ingredient calculated to produce the specific phenotypic result in association with the required physiological carrier. The specification for the novel dosage unit forms of the invention are dictated by and directly depend on the unique characteristics of the vector or vehicle used in the formulation and the limitations inherent in the art of compounding. The principle active ingredient (e.g. the adenoviral vector) is compounded for convenient and effective administration with the physiologically acceptable carrier in dosage unit form.

In one aspect of the invention, herein referred to as ex vivo processes, mammalian cells are (a) taken from a subject; (b) transfected or infected in vitro with the vectors and vehicles of the present invention comprising a DNA encoding a therapeutic protein, e.g. growth hormone, cytokine and/or cytokine inhibitor; (c) cultured in a suitable medium; and (d) autologously reimplanted. After reimplantation the subject's cells which have been transfected/infected with the vectors and vehicles of the present invention, produce the therapeutic proteins at the site of the bone pathology and effectuate healing of the bone pathology.

In another aspect of the invention, cells of a subject are transfected/infected in vivo locally at the site of the defect, for example, by injecting a physiological carrier compounded with the delivery vehicle of the present invention at the site of the defect.

In a preferred embodiment, only a single in vivo administration of the delivery vehicle of the present invention is necessary to achieve bone formation at the site of a bone pathology and effectuates healing and/or repair of the bone pathology. It is also contemplated that repeat administration may be necessary to effectuate sufficient bone formation for complete healing and/or repair of the bone pathology.

Administration of the delivery vehicles of the present invention does not destroy the integrity of the injured bone tissue. The local expression of osteoinductive factors at the site of the defect using the vectors and vehicles of the present invention results in accelerated new bone formation and repair of bone morphologies. In addition, no significant undesirable expression of the transgene is seen in other tissues (see FIG. 4).

Nonlimiting examples of bone pathologies which can be treated using the delivery vehicles of the present invention include osteoporosis, local or systemic bone mass loss, bone substance loss or bone structure disorders, bone fractures with bone substance loss, non-union fractures, defect fractures or pseudoarthrosis, bone defect conditions after an operation, Sudek's disease, bone substance loss after endoprosthesis loosening and periarticular osteolysis in diseases failing within the rheumatic category, e.g. rheumatoid arthritis and/or osteonecrosis.

In one embodiment the vectors and vehicles of the present invention which comprise a transgene encoding an osteoinductive factor, for example growth hormone, cytokine, growth hormone inhibitor or cytokine inhibitor, are useful for the acceleration of healing of transplants, particularly ligamentous, osseous or tendinous transplants, for example, in knee or shoulder surgery.

The vectors and vehicles of the present invention comprising a transgene encoding, for example, bone morphogenic protein 2–7 (BMP 2–7), transforming growth factor-β (TGF-β), fibroblast growth factors (FGFs), insulin-like growth factors (IGFs), platelet derived growth factors (PDGFs), vascular endothelial growth factor (VEGF), cytokines, and hedgehog proteins, e.g. Sonic hedgehog and Indian hedgehog, are also useful to improve bone structure.

In addition, the delivery vehicles of the present invention comprising a transgene encoding cytokine inhibitors, e.g. interleukin-1 receptor antagonist (IL-1Ra), sTNFαR (soluble tumor necrosis factor αreceptor) or interleukin-6 inhibitors, or resorption-inhibiting cytokines, such as interleukin-10, are useful to reduce bone degeneration, for example, in subjects suffering from osteoporosis.

Although indicated otherwise in U.S. Pat. Nos. 5,763,416 and 5,942,496 of Bonadio et al., bone-compatible matrices are contraindicated for use together with the delivery vehicles of the present invention. The use of a collagen gel bone-compatible matrix as a carrier for the vectors and vehicles of the present invention, was assessed by a histological study of bone defects generated in White New Zealand Rabbits, as described below in Example 3. A non-reabsorbed solid collagen structure was seen even 12 days after the administration of an adenoviral vector together with the collagen gel. From this it can be concluded that the adenoviral vector was encapsulated by the gel and hence had no possibility to infect the bone cells. Therefore, the use of a collagen matrix is contraindicated.

The delivery vehicles of the present invention are effective in the absence of a matrix possible due to the muscle surrounding the bone pathology which may serve as a natural matrix to guide the bridging of segmental defects. Indeed, BMP-2 is known to inhibit myogenic differentiation and to convert the differentiation of myoblasts into the osteoblast lineage. See Katagiri et al., *J. Ce. Biol.* 6:1755–1766(1993); Yamaguchi et al, *J. Cell. Biol.* 113: 681–687(1991). For the present invention, a matrix may particularly be unnecessary due to the local administration of the delivery vehicles of the present invention, the duration of transgene expression and the cell-mediated production of the osteoinductive factor.

The present invention is further explained in detail by reference to the following specific embodiments which are not intended to limit the invention.

EXAMPLES

Example 1

In Vitro Evaluation of an Osteoporosis Therapy with Retroviral Vectors on the Basis of Human Osteoblastic Cell Populations A. Materials and Methods Human Spongy Bone Isolation:

Human spongy bone was obtained from informed patients with therapeutic radial or ulnar resection osteotomy. Cells of arthritic femoral heads, often affected by necrotic changes, were difficult to cultivate and had only a short survival time in vitro.

Isolation of Cells:

After removal of the cortical parts, the remaining spongy bone was cut into pieces of about 1 mm$^3$ and then cultured. Fragments of residual cortical parts were treated overnight with 0.1% collagenase (Seromed, Berlin) in 25 cm$^3$ culture flasks (Nunc, Denmark). Thereupon the collagen solution was eliminated and the spongiosa fragments were washed 3 times with phosphate buffered saline (PBS; Seromed, Berlin). In this way the connective tissue cells released by the collagen digestion were quantitatively removed. The bone fragments were then cultivated in nutrient medium (RPMI medium 1640; GibcoBRL, Grand Island, N.Y.) with 10% fetal bovine serum (FBS) and 1% penicillin/streptomycin solution (GibcoBRL, Grand Island, N.Y.). The cells were cultivated in an incubator at 37° C. under 5% carbon dioxide gas treatment. After about 16 to 20 days the cells began to populate the surface of the spongiosa and the bottom of the culture flasks. After an additional 3 weeks the cells reached confluence and, after trypsinization with 2 mL of trypsin (trypsin, 0.25%; GibcoBRL, Grand Island, N.Y., USA) and the cells were divided between cell culture flasks and cell culture dishes.

Production of Retroviral Vectors:

The production of retroviral vectors was carried out in a cell line derived from the NIH3T3 cell line (CRIP). This cell line contains the retroviral env and gag genes integrated into the cellular genome. CRIP cells permit the production of retroviral vectors from proviruses. MFG-IRAP, which carries a DNA insert encoding the human interleukin-Is receptor antagonist (hIL-1Ra), and CRIP-BAG, which carries a DNA insert encoding the bacterial β-galactosidase gene (LacZ) and a neomycin resistance gene (neoR) for the selection of transfected cells, are described in the publication of Bandara et al., *Proc. Natl. Acad. Sci. USA* 90:10764–10768 (1993) under the title "Intraarticular expression of biologically active Interleukin-1-receptor-antagonist protein by ex vivo gene transfer", incorporated herein by reference. Both cell lines produce amphotropic retroviral vectors.

The viral long terminal repeat (LTR) serves as promoter for the hIL-1Ra-DNA and LacZ. The CRIP cells were cultivated in (DMEM) medium (GibcoBRL, Grand Island, N.Y.), 10% FBS (GibcoBRL, Grand Island, N.Y.) and 1% HERPES (GibcoBRL, Grand Island, N.Y.) in an incubator at 37° C. and 5% carbon dioxide gas treatment.

The viral vector-containing supernatant was collected daily from confluent cultures. After filtration through a fine 0.45 μm spray filter (Sartorius ASG, Germany) the supernatant was stored at −80° C. until use. MFG and BAG both originate from Moloney murine leukemia virus (MoMuLV, as described by Wehling et al., *Spine* 21:931–935 (1996) and by Wells et al., *Gene Therapy* 2:512–520 (1995)). MFG has previously been used as vector in various gene therapy experiments, including a human Phase-1 study in rheumatic arthritis. The retroviral vectors are replication-incompetent, which means that an independent proliferation of the retrovirus in vivo is not possible.

Infection of Cells:

The osteoblastic cells were removed from cell culture flasks by trypsin digestion and seeded into 12 well-plate cell culture dishes with 30,000 cells per dish. After attaining an approximately 80% confluence, the nutrient medium was removed and the cells were washed twice with 3 mL of physiological sodium chloride solution. The infection was carried out with 1 mL of viral vector supernatant at a concentration of $1 \times 10^6$ particles of retroviral vector per mL, and modulated with a cationic polymer, i.e. a copolymer of N, N, N',N'-tetramethyl-1,6-hexanediamine and 1,3-dibromopropane of Abbot Corporation, known under the name Polybrene®, (Aldrich, Milwaukee, Wis.). After the first hour of infection the cell culture dishes were slowly centrifuged at room temperature at 500 rpm and then incubated overnight under cell culture conditions. After 48 hours the MFG-IRAP-infected cells were collected and frozen at −80° for later IL-1Ra quantitation.

Detection of LacZ Infection:

48 hours after infection the cells were fixed and LacZ expression was detected by means of X-gal staining as follows: The cells were first washed with 1 mL PBS solution (Seromed, Germany) and fixed with Solution 1 (1 mL of 0.5% glutaraldehyde in 49 mL of PBS (Roth GmbH, Germany) for 10 minutes at room temperature. The cell culture dishes were then washed twice for 10 minutes each Solution 2 (1 mL of PBS solution in 1 mM magnesium chloride). Thereupon, Solution 2 was exchanged by the substrate solution (Solution 3) consisting of 1500 μL of 5 mM $K_3Fe(CN)_6$ and 5 mM of $K_4Fe(CN)_6$, 30 μL of 1 M $MgCl_2$, 750 μL of 1 mg/mL 5-bromo-4-chloro-3-indolyl-β-D-galactopyranoside (X-gal) and 27 mL of PBS, and left overnight in the cell culture dishes. Solution 3 was then replaced with PBS and the X-gal staining, as manifested by the typical blue colorations of the cells, was quantitated by optical microscopy.

Quantitation of IL-IRa Expression:

IL-1Ra expression was detected with a commercial ELISA kit (Biosource, USA) according to the manufacturers information.

Detection of Alkaline Phosphatase:

The alkaline phosphatase (ALP) was detected in the cell cultures in the first passage. Immortalized synovial fibroblasts (HIG-82) served as negative controls; immortalized bone marrow stem cells of osteogenesis imperfecta mice (OIM), which were previously stimulated with recombinant BMP-2, served as positive controls. All cell cultures were subjected to a triple freeze-thaw cycle at −80° C. in order to disrupt the cell membranes. The burst cells were then stored at a temperature of −80° C. until further analysis. The alkaline phosphatase activity was detected with a commercial analysis kit available from Sigma Diagnostics (Dorset, United Kingdom) according to the manufacturer's instructions and measured photometrically at a wavelength of 405 nm after 1, 2 and 30 minutes, using a UV-Max instrument (Molecular Devices, USA).

B. Results

X-gal Staining:

The infection with retroviral-LacZ was carried out in three cell culture dishes simultaneously. In all cell culture dishes a blue coloration of the cells was obtained by the X-gal staining. The proportion of infected cells in the total cell count according to optical microscopic quantitation was 60%. No selection of the infected cells was carried out.

Gene Expression:

Infection of the cells with retroviral-IRAP was carried out in 6 cell culture dishes. ELISA analysis of the supernatant from all 6 cells showed that the cell populations were infected with DNA encoding hIL-1Ra and that the hIL-1Ra was expressed with an average of 9111.5 pg per 50,000 cells and 48 hours at a standard deviation of 522.4 pg (see FIG. 1). ELISA analysis of the supernatant of the three culture dishes with non-infected cell cultures gave negative values, as shown in FIG. 1.

Detection of Alkaline Phosphatase:

Alkali phosphatase (ALP) is one of the first markers endogenously synthesized by immature osteoblasts and during the osteoblastic maturation process. The cell populations used in this experiment spontaneously expressed alkaline phosphatase with a mean value of 9.5 units per 1,000,000 units, at a standard deviation of 0.7 units. As shown in FIG.

2, the immortalized synovial fibroblasts (HIG-82) serving as negative controls expressed no ALP; in contrast to the BMP-2-stimulated immortalized OIM cells, which did express ALP and served as positive controls. Chosen as control cell populations were OIM and HIG-82 cells, since the power of OIM cells to synthesize ALP after stimulation with rhBMP-2 ALP is well known. Because of their ability to synthesize ALP the OIM cells were rated as an osteoblastic cell population.

Example 2

Use of Adenoviral Vectors for Developing a Therapy of Estrogen-Deficiency Induced Osteoporosis in the Balb/C Mouse Model A. Materials and Methods The basis of these experiments was the well-known knowledge that estrogen deficiency leads to activation of osteoclasts by systemic increase of the cytokines interleukin-1 and TNF-α, which, through increased osseous resorption, causes generalized bone mass loss. The theory behind the experiments evaluating an osteoporosis therapy on the Balb/C mouse is that, as is known, ovarectomy is followed by generalized bone mass loss which reaches its maximum after about two weeks. See Kishi et al., Bone 22:515–22 (1998). At the time of the experiments all experimental animals were 6 weeks old. A total of five different experimental series was carried out.

The urinary excretion of deoxypyridinoline crosslinks after ovarectomy (OVX) and after sham ovarectomy was measured after 2 days. The analysis of crosslinks was done by means of the commercial kit of Metra Biosystems Inc. (CA, USA) according to the manufacturer's instructions. This experimental series was used for evaluating the effect of ovarectomy on bone resorption and for testing the suitability of this analysis for differentiation of the bone mass loss after treatment with therapeutic vectors.

E1/E3 adenoviral vectors, comprising a DNA encoding the marker LacZ (Ad-LacZ) were used to infect bone and bone marrow cells to determine the efficacy of transgene expression therein. The vectors were administered intrafemorally through a transcutaneous intracondylar access, which made it possible to administer 100 µL of a suspension with physiological sodium chloride solution and $10^9$ pfu of Ad-LacZ by the intraosseous route. Controls were carried out with the instillation of physiological sodium chloride solution alone. The immunohistochemical staining method for LacZ, described herein, makes possible the detection of successfully infected cells stained by X-gal manifested by an intensive blue coloration of the LacZ-expressing cells.

In addition, the duration of gene expression and the intracorporeal distribution of vectors after intraosseous vector administration was investigated on the Balb/C mouse model by the administration of adenoviral markers which code for the marker enzyme luciferase. Three mice each were sacrificed on Day 2, 14 and 21 after vector administration and different tissue types in the region of the injection as well as different internal organs were analyzed for expression of LacZ. The enzyme activity of the luciferase was measured photometrically with the Autolumat® LB953 (Berthold Co., Germany) as described below in Example 3.

The intraosseous vector administration, more commonly carried out in the experiments, was compared with parenteral vector administration, in order to investigate the duration and intensity of systemic expression levels in both procedures. Intraosseous administration of the vectors was carried out intrafemorally, as described above, whereas the parenteral injection was carried out via the retroorbital sinus which is generously dimensioned in the mice. The systemic IL-1Ra levels were determined in the murine serum after repeated blood withdrawals from the retroorbital sinus. The blood withdrawals took place before vector administration and then on Days 1, 2, 3, 5, 9 and 12 after injection of the vectors. The IL-1Ra levels were analyzed with commercial ELISA kits according to the manufacturers instructions.

To investigate the therapeutic effectiveness of adenoviral vectors comprising a DNA encoding IL-1Ra for ovarectomy-induced bone mass loss, four groups of at least 8 mice each were made up, with ovarectomy performed in 2 groups. The mice received either the Ad-IL-1Ra or Ad-LacZ. The two remaining groups were treated in the same way, except, instead of the ovarectomy, only a sham operation was carried out. The analysis was done by measuring the total dry weight of the non-manipulated humeri, tibiae and fibulae, in order to be able to evaluate the systemic effect of the vector administration. The dry weight was measured in mg after exarticulation and complete defleshing of the bones and treatment of the bones in a 90% acetone-alcohol bath.

B. Results

Figure 6:
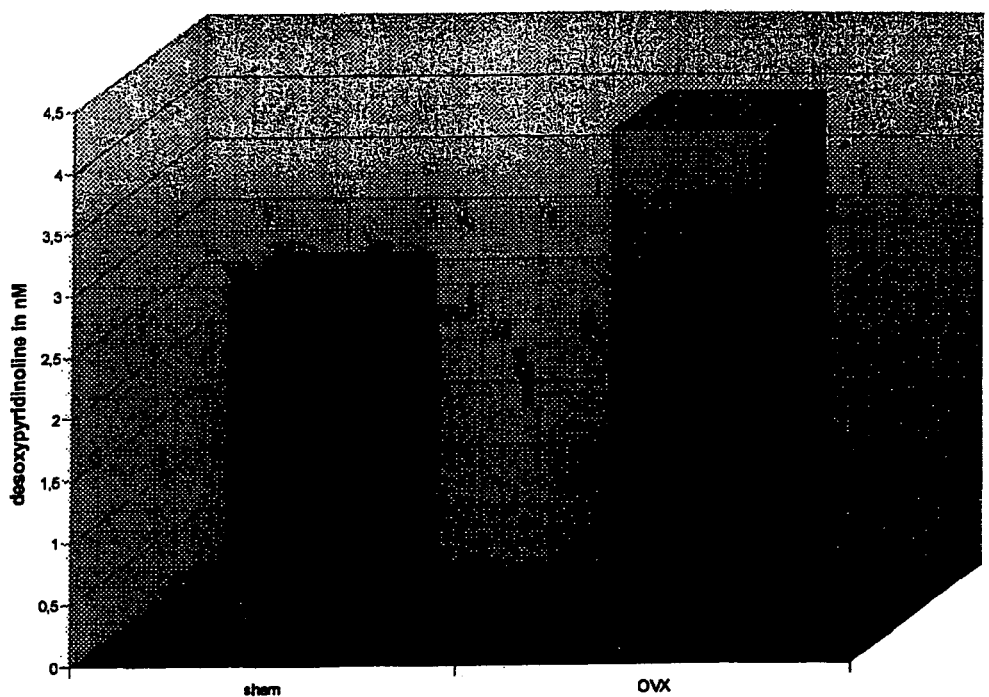
FIG. 6 shows the amount of deoxypyridinoline crosslinks (nM) excreted in the urine after ovarectomy (OVX) and sham ovarectomy in white Balb/C mice. It is clear that after ovarectomy there is a greater urinary excretion of deoxypyridinoline crosslinks, which serve as a direct osteoclastic activity parameter.

As shown in FIG. 6, analysis of the urinary excretion of deoxypyridinoline crosslinks confirms that ovarectomy is followed by an increase of osteoblastic activity with increasing bone resorption, indicating that the ovaretomized Balb/C mouse is a suitable model for determination of the bone mass loss and for the evaluation of transgene expression on estrogen-deficiency-induced osteoporosis.

Figure 7:
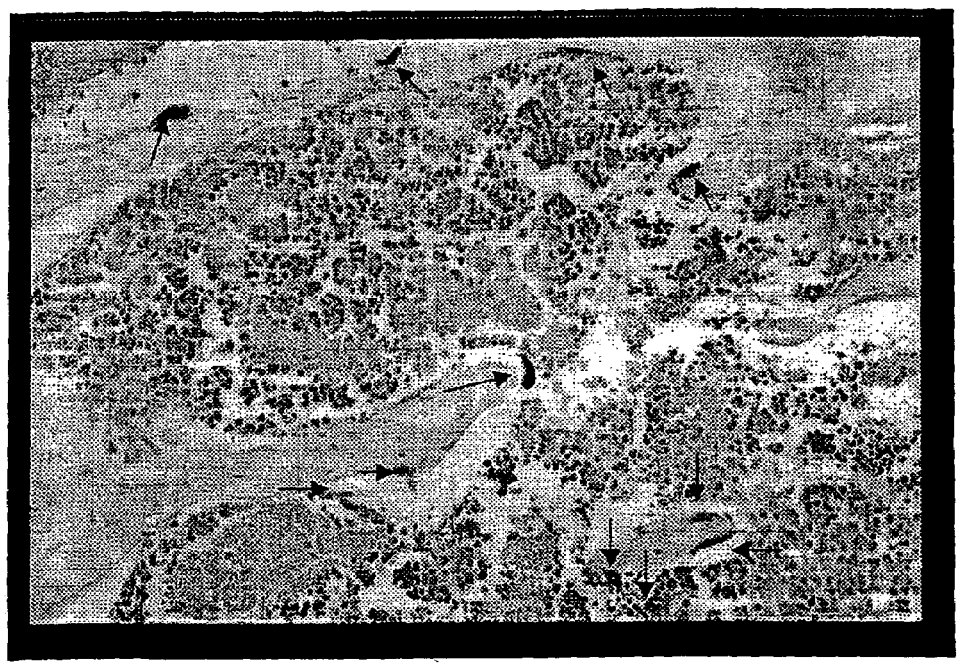
FIG. 7 is a 50-fold enlarged view of a paraffin section of the intrafemoral cavity of Balb/C mice after intraosseous transduction with $10^9$ pfu of adenoviral vectors which comprise a DNA encoding LacZ (β-galactosidase). Morphologically, lining osteoblasts and also bone marrow cells are mainly transduced. These cells are marked by arrows.

As shown in FIG. 7 (indicated by arrows), intraosseous administration of adenoviral vectors successfully transduces a number of different cell types. According to immunohistochemical X-gal staining, osteoblasts are predominantly infected, as well as bone-marrow cells.

Figure 4:
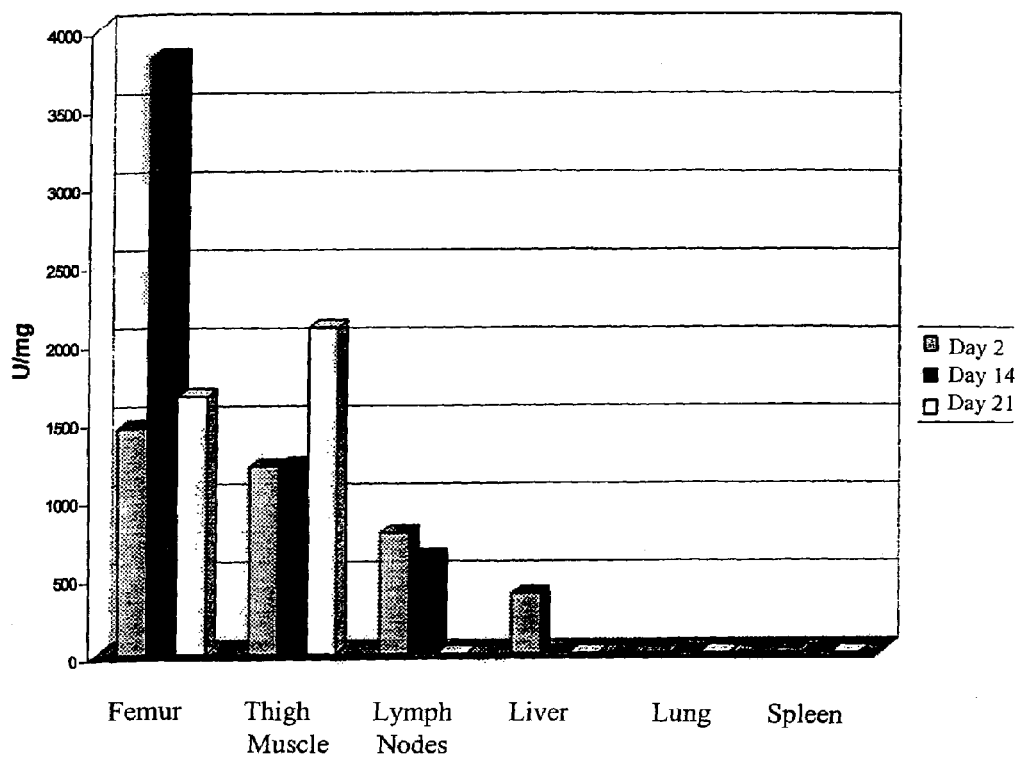
FIG. 4 is a plot of the expression of the marker enzyme luciferase (units/g) in white Balb/C mice in bone tissue, muscle tissue, lymph node tissue and in the liver after intraosseous/intramuscular transduction of the femora with $10^9$ pfu Ad-Luc. Lungs and spleen are apparently not reached by the adenoviral vectors and show no enzyme expression. In bones and musculature the enzyme expression lasts for the entire 21-day period of the investigation; in the liver an expression is only detectable for 5 days, and in the draining inguinal lymph nodes for 14 days. Thus, outside the area of administration a slight and temporally very limited transgene expression can be assumed.

The enzyme activity of luciferase after intraosseous vector administration of Ad-Luc is shown in FIG. 4 which shows that the expression in bone and musculature persists over the entire 21-day study period. Luciferase expression in the liver (2 days) and draining lymph nodes (14 days) is transient and does not attain the level of enzyme activity in the injection area.

Figure 5:
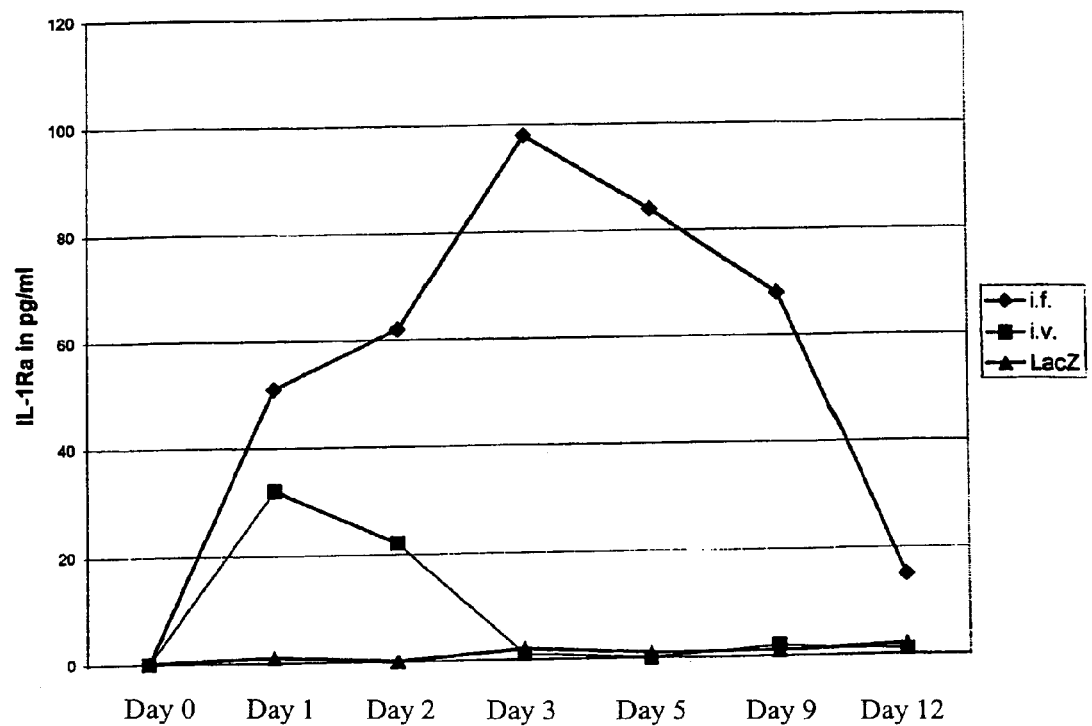
FIG. 5 shows the systemic detection of IL-IRa (interleukin-1 receptor antagonist protein) over a period of 12 days in white Balb/C mice, for testing the quality of different forms of administration of AD-IL-IRa in systemic bone diseases. After intrafemoral administration (♦) of $10^9$ pfu of Ad IL-1Ra, positive systemic IL-IRa levels are found for the whole 12-day study period with maximum values on Day 3 of nearly 100 pg/mL. In contrast, on intravenous administration of Ad-IL-1Ra (●), lower values down to 32 pg/mL are attained, and a maximum duration of expression of 3 days. In the negative control carried out with $10^9$ pfu of the non-therapeutic marker gene Ad-LacZ (▲) no IL-1Ra could be detected systemically.

FIG. 5 shows the comparison of the intravenous and intrafemoral vector administration. The intrafemoral form of administration is preferred to the intravenous form of administration since, with regard to both intensity of expression of transgenes and duration of expression the intrafemoral form of administration is more effective (FIG. 5).

Figure 3:
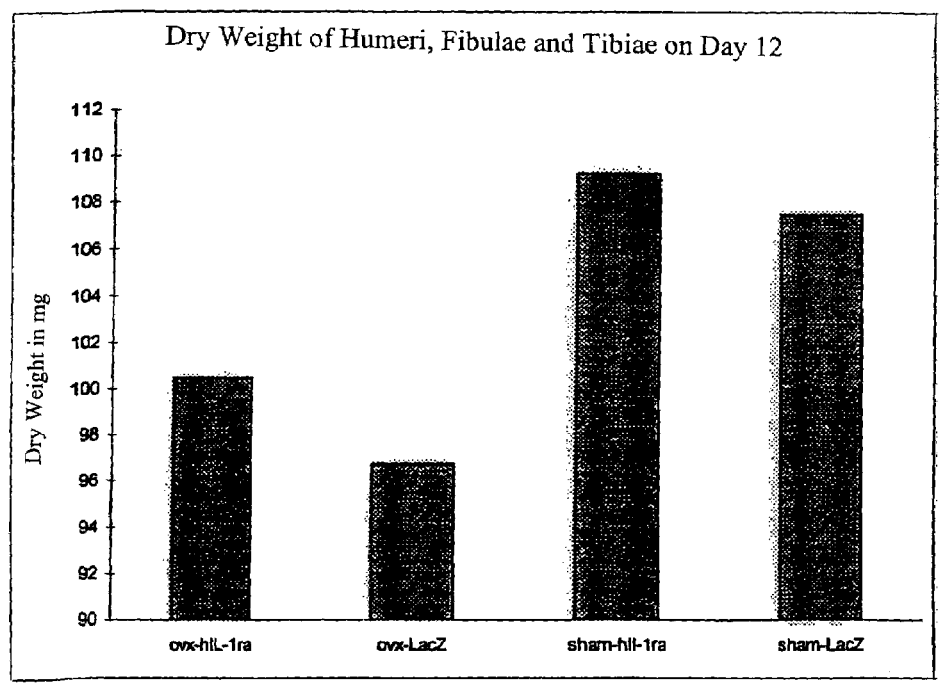
FIG. 3 is a plot of the decrease of the dry weight of the humeri, tibiae and fibulae in milligrams (mg) in ovarectomized (OVX) white Balb/C mice 12 days after surgery, in comparison to sham-operated mice. By intraosseous administration of $10^9$ pfu of Ad-IL-1Ra (OVX-IL-1Ra) the bone mass loss could be reduced by about 50% compared with the untreated control group (OVX-LacZ).

FIG. 3 demonstrates, on the basis of the dry weights (mg) of humeri, tibiae and fibulae, that the ovarectomy-induced bone mass loss, expressed here as weight of mineralized bone, can be reduced by about 50% by the use of adenoviral vectors comprising a DNA encoding IL-1Ra.

Example 3

Treatment of Bone Defects in New Zealand Rabbits

A. Material and Methods

Animals:

White female New Zealand rabbits older than 6 months and weighing from 4.3 to 5 kg were used in this study. In all animals, surgical defects were produced in the femur in such a way (as described below) that, without treatment, these defects did not heal after 9 weeks.

Surgical Procedure:

After introduction of general anesthesia with ketamine hydrochloride (Ketaject®) (40 mg/kg/M) and xylasin (Xylaject®) (3 mg/kg/M) is. m., both femura of the rabbit were shaved, disinfected with isopropyl alcohol and prepared in a sterile manner. A general anesthesia was introduced with the use of Isofluran 0.8 to 1.5% (AErrane®) supplemented with 50 to 100% oxygen and 50% dinitrogen oxide. Additional local anesthesia with 2% lidocaine was applied, while the periosteum was detached from the femora, since this procedure caused movements of the rabbits even under general anesthesia. This was followed by a longitudinal preparation of the soft parts. The entire diaphysis of the femora was prepared and the periosteum layer was completely eliminated. A 7-hole DCP plate (Synthes, Colo., USA) was then placed above the lateral femora and fixed with 2.7 mm self-cutting screws. An exact defect of 1.3 cm was produced by means of a ball miller. In order to protect the osteosynthesis postoperatively from the enormous bending forces during "kicking" of the rabbits, 3 cerclage wires were used, to effect an additional fixation over the plate at the distal and proximal ends of the femora. To completely eliminate bone fragments and bone marrow parts, several rinses were carried out with physiological sodium chloride solution. By re-fixing the musculature around the femoral defect, a defect chamber was created. All soft layers were very carefully and accurately closed, and the skin was sutured intracutaneously. No further splint or cast was necessary.

Vectors:

For the infection of the cells, a first-generation recombinant E1/E3 deleted adenoviral vector was used, into which the LacZ (Ad-LacZ) gene or the luciferase gene (Ad-Luc) had been inserted into the E1 region. In each case a human early promoter was operatively linked to the gene. For each defect, 0.5 mL of a suspension of $1 \times 10^{10}$ particles of adenoviral vectors were injected, either in suspension with a physiological sodium chloride solution or with purified collagen gel (Vitrogeng®, Collagen Corporation, Palo Alto, Calif.). The contralateral femoral defects received either 0.5 mL of physiological sodium chloride solution or 0.5 mL of collagen gel without virus particles.

The vectors Ad-LacZ and Ad-Luc were propagated in 293 cells described by Graham et al., *J. Gen. Virol.* 36:59–72 (1977). The 293 cells were in each case transfected with adenovirus for 2 hours with a multiplicity of infection (m.o.i.) of 10. The cells were harvested after they were scraped off 36 to 48 hours after the infection and resuspended in 5 mL of a 50 mM Tris-Cl (pH 7.5) and 200 mM sodium chloride. After 5 freeze-thaw cycles the viral vectors were purified with 2 cesium step gradients (4° C., 30,000 rpm, 1 hour). Ad-LacZ was dialyzed against 10% glycerol dialysis buffer (100 mM sodium chloride, 10 mM Tris-Cl, pH 7.5; 1 mM magnesium chloride, 10% v/v glycerol), as described by Mittereder et al., *J. Virol.* 70:7498–7509 (1996), and Ad-Luc was dialyzed against 3% sucrose dialysis buffer (150 mM sodium chloride, 10 mM Tris Cl, pH 7.5; 10 mL of magnesium chloride, 3% v/v of sucrose). Each vector was titrated through its optical density of 260 nm. The vector stocks were stored until used at a concentration of $7 \times 10^{12}$ particles per mL at −80° C.

Groups, Data Collection and Analysis:

Group 1: The femoral defect was created in 4 rabbits treated with 0.5% physiological sodium chloride solution, which received $1 \times 10^{10}$ particles of Ad-LacZ. Two rabbits were sacrificed two days after the operation, and the other two rabbits were sacrificed 12 days after the operation.

Group 2: Four rabbits were treated with a mixture of 0.5 mL of collagen gel (Vitrogen®) and $1 \times 10^{10}$ particles of Ad-LacZ. The rabbits were sacrificed according to the schedule of Group 1.

Bone marrow, cortical and trabacular bone, scar tissue which fills out the defect, and muscle were analyzed for LacZ expression by means of X-gal staining of all rabbits of Group 1 and 2. To determine whether a systemic distribution of the vectors had taken place, tissues from the spleen, liver and lung were analyzed as well as bone, bone marrow and muscle from the contralateral untreated segmental defects. All tissue parts were fixed in 10% formaldehyde solution for 24 hours, then decalcified in 20% EDTA, which took 2 to 3 weeks with a weekly exchange of the EDTA. After embedding the demineralized tissue in paraffin, blocks were cut and the tissue sections stained with X-gal and eosine. The infected cells were evaluated histomorphologically.

Group 3: Eight rabbits were treated with 0.5 mL of a mixture of physiological sodium chloride solution and $1 \times 10^{10}$ Ad-Luc particles. The rabbits were sacrificed 2, 5, 10 and 14 days after the operation. Tissue samples were taken of (1) the trabacular and cortical bone which surrounded the defect chamber, (2) connective tissue which filled the defect chamber, and (3) muscle which surrounded the femoral defect. To verify a systemic distribution of the vectors, lung, liver and spleen samples were analyzed together with musculoskeletal samples of the non-infected contralateral defect. All tissue samples were homogenized, 0.1 mL of physiological sodium chloride was added and the samples were subjected three times to a freeze-thaw cycle, in order to disrupt the cells. The cells were then stored at −80° C., until measurement of the luciferase activity was conducted. After the last thawing the samples were centrifuged at 10,000 rpm (5600×g) for 5 minutes, and the supernatant solution was set aside for measurement of the luciferase activity. The luciferase activity was measured at room temperature by means of an AutoLumat® LB953 (Berthold Co., Germany) according to the manufacturer's instructions.

For histological analysis, undecalcified sections were stained with the Von Kossa stain after plastic embedding with Technovit® 7200 VLC (F. Kulzer, Norderstedt, Germany), and cutting of 300 μm sections with a diamant-coated saw (Exacts Fa. Messner, GmbH, Norderstedt, Germany). The sections were made parallel to the long axis of the bone, extending over the entire length of the defect.

B. Results

Figure 9:
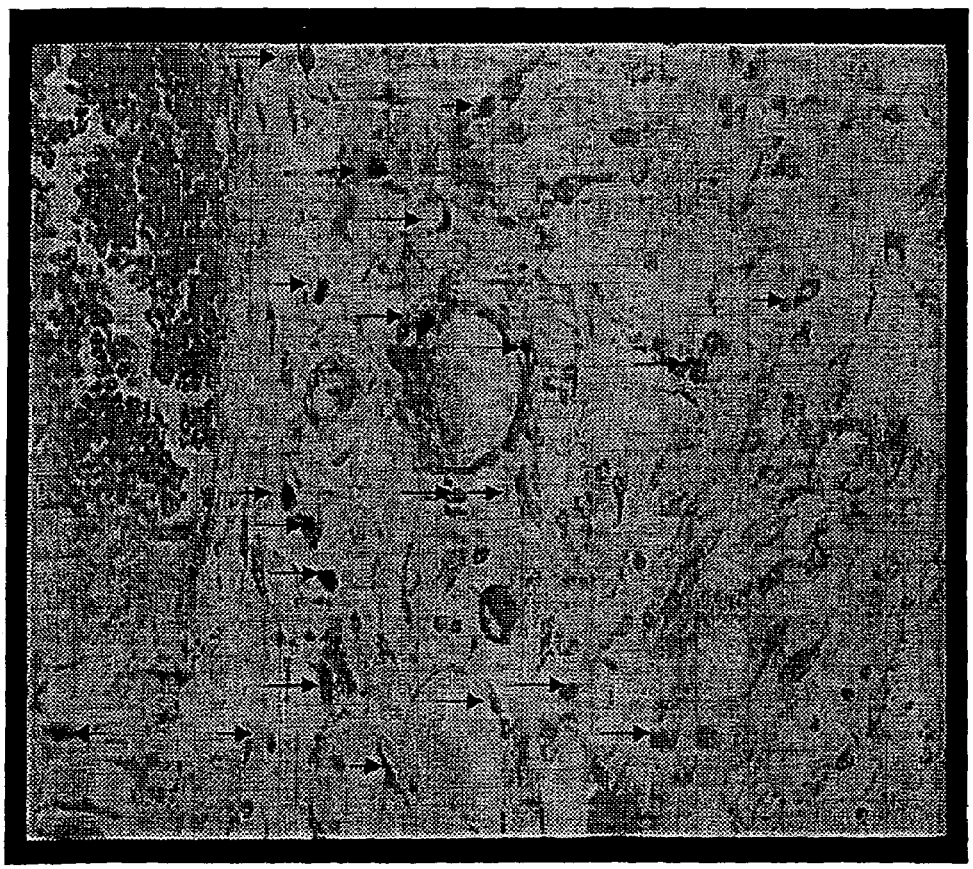
FIG. 9 is a 50-fold enlargement of a decalcified paraffin section from the region of the femoral defect in the white New Zealand rabbit. Morphologically, not only connective tissue cells but also adipocytes and possibly stem cells are transduced, marked by arrows.
Figure 10:
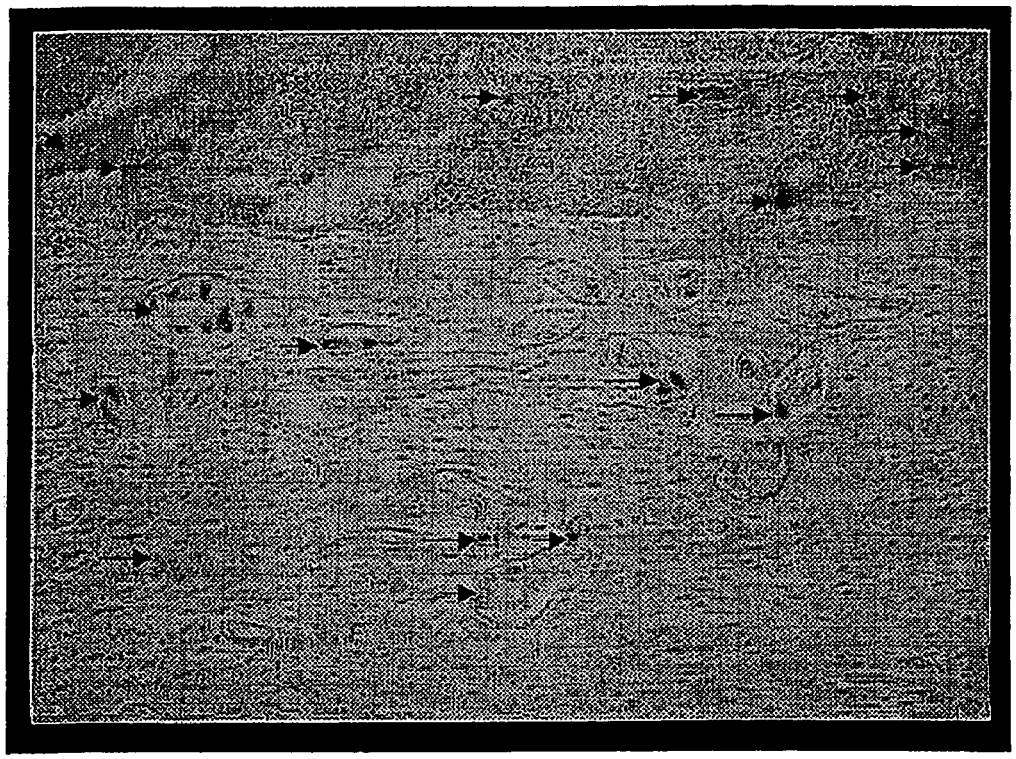
FIG. 10 is a 20-fold enlargement of a decalcified paraffin section from the region of the edge of defect in a femoral defect model of the white New Zealand rabbit. Histomorphologically, not only lining osteoblasts indicated by arrows are transduced, but also connective tissue cells of the adjacent scar.

X-gal Staining:

Histomorphological analysis showed that the production of Ad-LacZ, which was suspended either in physiological sodium chloride solution or in collagen gel, led to local infection of bones, bone marrow, scar tissue and callus tissue, as well as to infection of the muscle surrounding the injection site (FIGS. 9 and 10). By contrast, no LacZ cells were found in the lung, liver or spleen, nor in the contralateral femoral defect. The use of collagen gel as carrier for the adenoviral vector was assessed by a histological study of the defect and the scar tissue which filled out the opening. A non-readsorbed solid collagen structure was seen even up to 12 days after the operation. From this observation, it was concluded that the adenovirus has been encapsulated by the gel and hence had no possibility for transduction. Therefore the use of a collagen matrix for gene delivery is contraindicated. The histological analysis showed no evidence of local inflammation.

Figure 8:
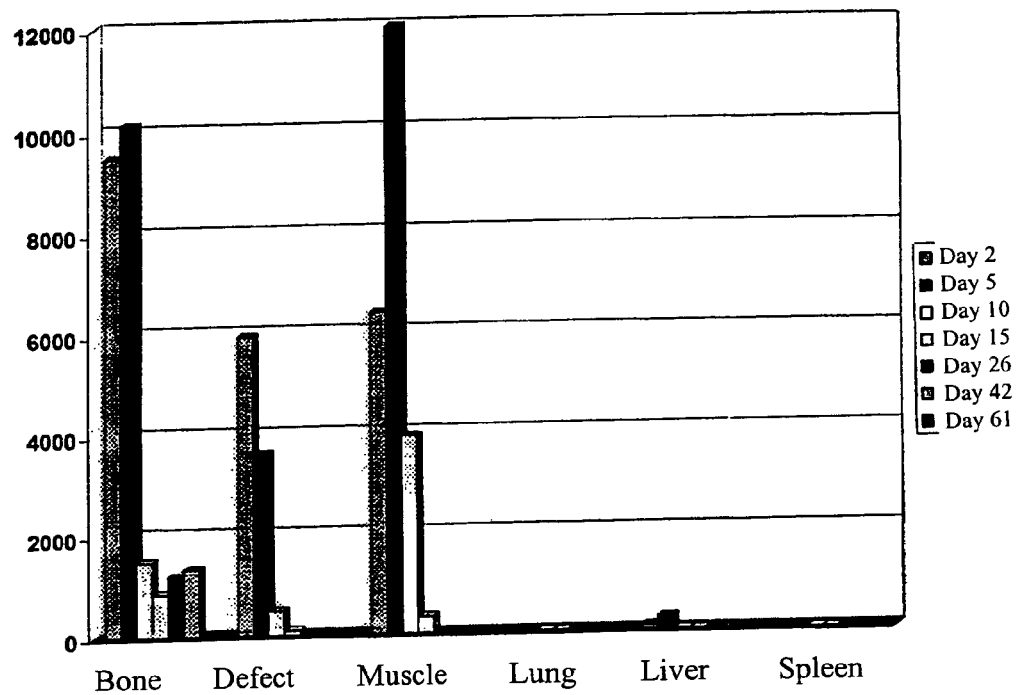
FIG. 8 is a plot of the expression of luciferase (units/µL) after injection of $10^{10}$ pfu of Ad-Luc into the femoral defect in white New Zealand rabbits. The distribution pattern of the enzyme activity shows that after local vector administration into the bone defect the expression of the luciferase apparently takes place mainly from local tissue structures. Bones, defect/scar tissue and musculature express luciferase with high expression values (up to 70,000 units/100 µl in muscle). No detection of luciferase activity is found in the lung, spleen and contralateral musculoskeletal tissue samples. Only in the liver can a transient, weak luciferase activity be detected for 5 days. The luciferase expression in the bone was detectable at the longest for a total of 42 days, while in the defect-filling tissue and in the musculature, luciferase expression was no longer detectable after 15 and 26 days, respectively.

Luciferase Assay:

Different luciferase activities were found in the bone and bone marrow, as well as in the defect-filling connective tissue, and in the surrounding muscle tissue at the injection site. Five days after infection, a slight luciferase activity was noted in the liver, an activity which completely disappeared after 10 days (FIG. 8). No luciferase activity could be found in the contralateral femur, lung and spleen (FIG. 8).

Figure 11:
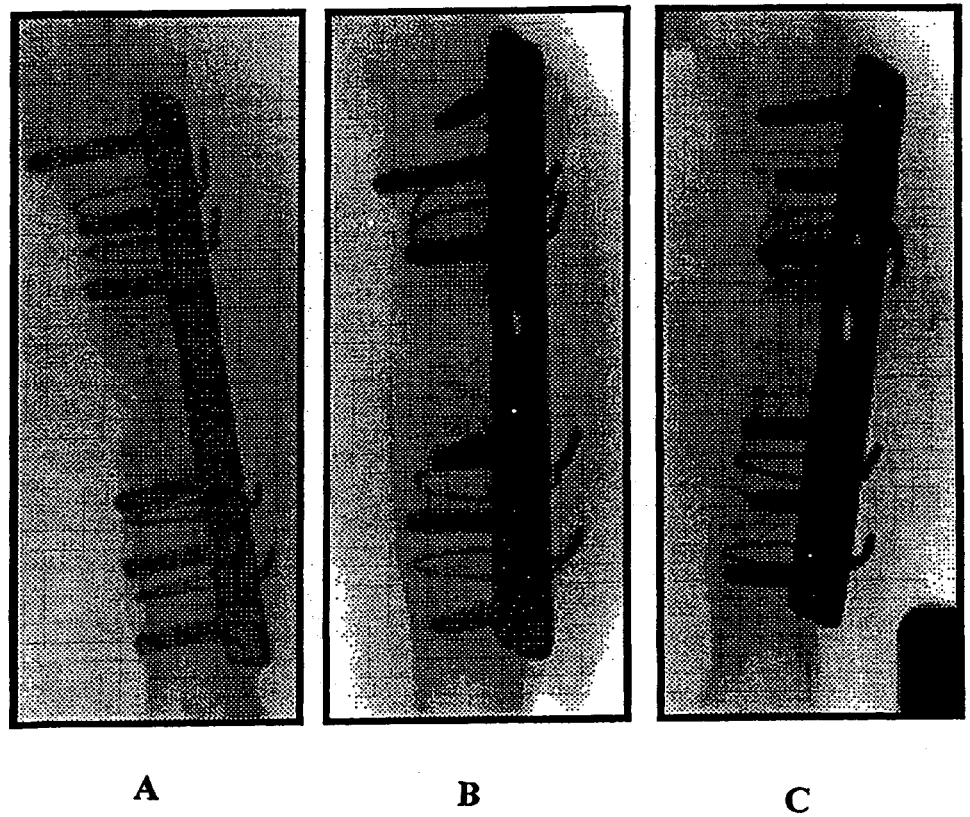
FIG. 11 shows three X-ray pictures of the course of healing of the femoral defect in the white New Zealand rabbit 5 weeks after intralesional transduction with $2\times10^{10}$ pfu of adenoviral vectors comprising a DNA encoding BMP-2. Clearly visible in all three cases is a nearly complete filling of the defect chamber with mineralized bone.
Figure 12:
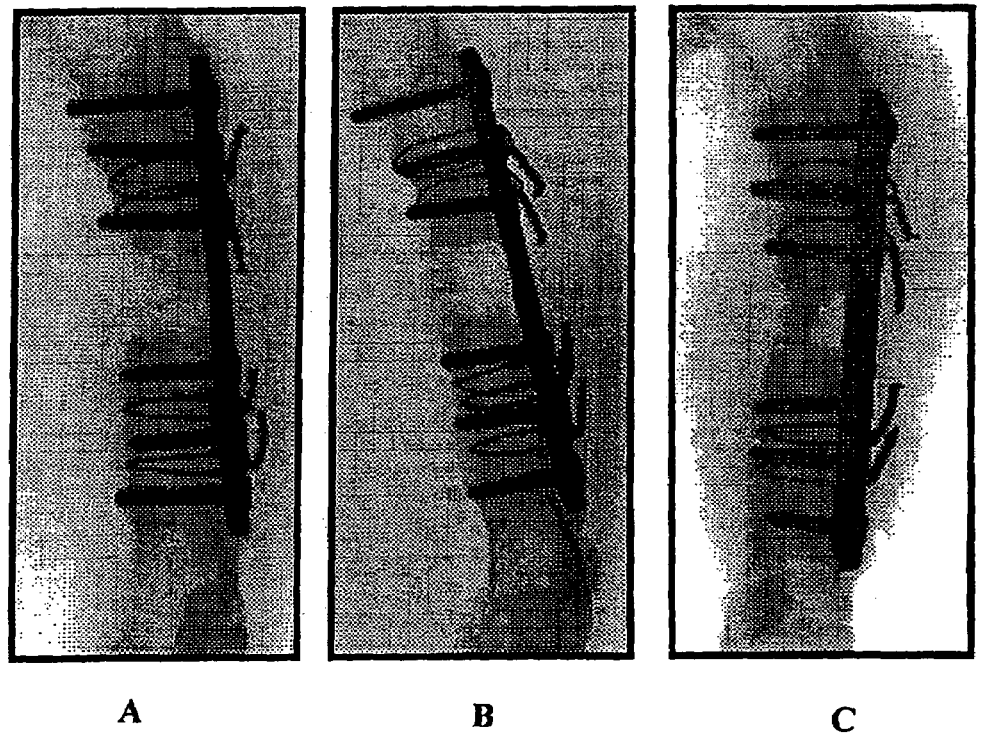
FIG. 12 depicts three X-ray pictures which show the course of healing of the femoral defect in the white New Zealand rabbit 5 weeks after intralesional infection with $2\times10^{10}$ pfu of an adenoviral vector comprising a DNA encoding the nontherapeutic marker gene luciferase. Distinct osseous substance defects can be seen in the defect chamber. Comparison with the course of healing after administration of therapeutic vectors comprising a DNA encoding BMP-2 (FIG. 11) testifies to the healing effects of the vectors of the present invention.
Figure 13:
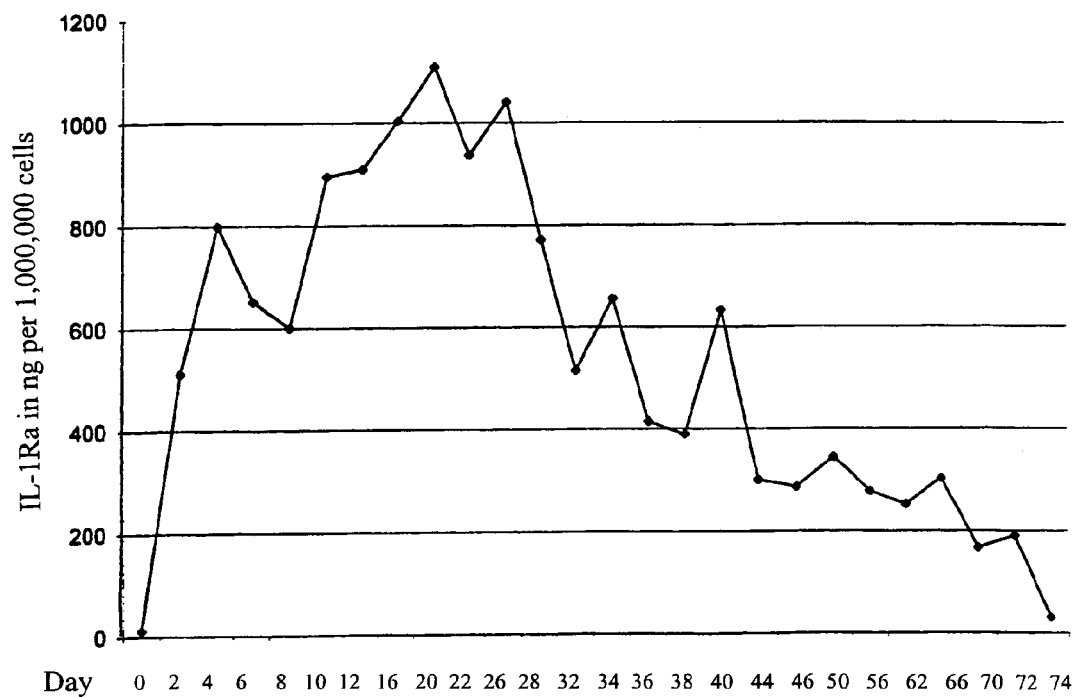
FIG. 13 shows a production of human IL-1 Ra osteoblast cells following in vitro transduction with Ad-IRAP after a multiplicity of infection of 1000. The highest degree of expression was noted 3 weeks after the transduction. The gene expression was detectable in vitro for 72 days.

Radiological Course of Healing after Administration of Therapeutic Genes:

Since the preliminary studies with which the detection of the transduceability of the different musculoskeletal tissue structures was performed and the duration of expression of transgenes was determined, the femoral defect model of the white New Zealand rabbit was considered a suitable model for evaluating the effect of genes encoding biologically active osteoinductive proteins on healing of the defect. Four and six rabbits each were infected according to the same procedure described above with $1\times10^7$ pfu of Ad-TGF β and $2\times10^{10}$ pfu of Ad-BMP-2, respectively, simultaneously with four and five control rabbits of the same age, which were infected with the Ad-Luc. X-ray controls were carried out at two-week intervals after the first control investigation done one week after the operation. In the group to which Ad-BMP-2 had been administered, a distinct mineralization spur relative to the control group was visible after 5 weeks, as shown in FIGS. 11 and 12. Final radiological examination in week 12 showed good osseous buildup of the femoral defect chamber in all 6 rabbits treated, while there was a deficient buildup ranging all the way to pseudoarthrosis, in the nontreated control group. A similar trend was also noted in the group to which Ad-TGFβ has been administered. In comparison to the control group, the radiological course of bone repair showed distinctly more mineralized substance in the femoral defect chamber, but without the formation of a radiologically visible ossification in the sense of corticotrabecular maturation. This result remained unchanged up to the 18th postoperative week.

In summary, it may be concluded that Ad-BMP-2 had a stimulating effect on ossification in the femoral defect; while, Ad-TGFβ apparently has a greater enhancing action on nonspecific mineralization of the tissue without leading to ultimate maturation of the bone. A combination of the two vectors may optionally lead to a further acceleration of bone fracture healing in defect situations.

Biomechanics:

12 weeks after the operation and infection with the viral vectors into the defect site, the six rabbits which received Ad-BMP-2 ($2\times10^{10}$ pfu) and 5 control rabbits which received $2\times10^{10}$ pfu Ad-Luc, were sacrificed. The operated femora were extensively de-fleshed, sparing all ectopic bone bridges. This was followed by careful metal removal. In doing so, it was found that one femur of the control group healed in the form of connective-tissue pseudoarthrosis, a second femur of the control group only showed such a thin bone bridge that it broke even upon very careful preparation. Hence this femur was excluded from the evaluation. After removal of all metal, the preparations were frozen at −80° C. until further analysis.

The biomechanical analysis was carried out by the three-point bending procedure in order to determine the flexural stiffness and maximum bending force of the femora.

The femora were stored in the frozen state until 24 hours before the test, and then slowly thawed in the cooling chamber. Each femur was placed in the three-point bending system that assured a free bending distance of 4.5 cm. The load was applied in posterior-anterior direction, with the load transmitted at the midpoint of the free bending distance which in all cases represents approximately the midpoint of the diaphyses.

The tests were carried out with the Instron 8500 servo-hydraulic testing system (Instron Corp., Canton, Mass.); an Instron 2500 lbf load-uptake cell was used. The deformation of the femora was measured with an internal LVDT system. The data were recorded by means of Instron's MAX software and analyzed with the MS-Excel software program.

A maximum bend of 1 cm was applied, at a bending rate of 0.5 cm/min or 0.0833 mm/sec. The test was ended when the femora fractured.

The test group which received Ad-BMP-2 showed a significant difference (p=0.036) relative to the control group with regard to stiffness and also with regard to the force applied (p=0.0055).

| Individual measurements: | | | |
|---|---|---|---|
| Stiffness | | Force | |
| Ad-BMP-2 | Control | Ad-BMP-2 | Control |
| 75.6000 | 80.8000 | 195.0000 | 102.0000 |
| 118.0000 | 64.0000 | 131.6000 | 103.2000 |
| 99.6000 | 53.2000 | 171.2000 | 82.0000 |
| 79.6000 | 0.0000 | 227.6000 | 0.0000 |
| 97.6000 | | 206.4000 | |
| 45.6000 | | 92.4000 | |

The mean bending strength of specimens derived from rabbits infected with an adenoviral vector comprising a DNA encoding BMP-2 (170.7+/−24.4N) was significantly higher than the control specimens infected with an adenoviral vector comprising a DNA encoding luciferase (70.8+/−24.4 N). These findings were supported by the results of the testing of diaphyseal stiffness. The bending stiffness of the femora infected with AdBMP-2 was significantly higher (84.0+/−10.2 N/mm) than the stiffness of the femur infected with AdLuc (49.5+/−17.4 N/mm).

The biomechanical analysis according to the three-point-bending procedure suggests that the use of the adenoviral vectors which comprise a DNA encoding BMP-2, can bring about an acceleration of bone defect healing.

Histomorphometry:

As in the above-described experiments the femoral defect model of white New Zealand rabbits was used. 16 weeks after operation of the animals and after infection with $10^7$ pfu of adenoviral vectors comprising a DNA encoding TGFβ (Ad-TGFβ) the animals were sacrificed and prepared. Serving as control group were 4 white New Zealand rabbits which received only $10^7$ pfu of an adenoviral vector comprising a DNA encoding luciferase (Ad-Luc).

Pictorial analysis was carried out on the digitalized histologic section as follows: The pictures were made sharper with a 2-fold band filter in order to define the blue-colored osseous areas (Trichrome staining). Osseous areas were defined by the color-cube technique (3×3 pixel), after standardizing against the normal cortical bone outside the defect. The previous defect boundaries were digitally marked and the former defect area (area of interest AOI) was analyzed for intensity of the blue coloration.

Four different measurements were carried out:

1. Absolute bone mass in the AOI;

2. Mean light intensity—measurement of the intensity of coloration makes it possible to draw conclusions regarding the quality of the newly formed bone;

3. Mass of mineralized tissue relative to the size of the defect, in percent; and 4. IOD (integrated optical density, corresponding to the mean optical light intensity per surface area measured).

Determined as AOIs were the following analyzed zones:

1. Total area from the distal to the proximal screw hole;

2. Bone neoformation along the removed DCP plate;

3. Bone neoformation of the corticalis opposite the removed DCP plate; and

4. Sum of defect edges.

In the test group to which Ad-TGFβ was administered, the total mass of mineralization in the defect region was more than twice as large as in the control group ($19.5 \pm 10.7$ mm$^2$ versus $9.04 \pm 4.3$ mm$^2$). Even more marked were the differences when the surface area and light intensity (IOD) were taken into consideration ($1754.0 \pm 906.0$ mm$^2$ versus $557.7 \pm 138.0$ mm$^2$). However, even in this case, the difference in the t-test for unconnected samples was not significant, which is explained by the great dispersion at small case numbers.

However, the results unequivocally indicate that TGFβ, produced and expressed on a cellular level, has a positive effect on mineralization and ossification after defect fractures. By using the technique of gene transfer with subsequent expression of the growth factor, which, as described in the preliminary experiments, represents a predominantly local process, the well-known side effects of systemic TGFβ administration may be prevented.

The histology of the undecalcified femur confirmed that infection with an adenoviral vector comprising a DNA encoding BMP-2 at the site of the femur defect led to complete ossification across the entire defect after eight weeks (FIG. 11). Von Kossa staining showed complete recreation of cancellous bone and early6 transformation to cortical bone in the femur defect area. In contrast, the defect area of the control femur infected with an adenoviral vector comprising a DNA encoding luciferase was dominated by an extended central fibrosis, surrounded by cloudy new bone formation and only a faint connection of the distal and proximal femoral segment along the DCP-plate (FIG. 12).

Impressively, a single administration of the adenoviral vectors of the present invention was sufficient to achieve complete healing of the femur defects in New Zealand White Rabbits. Furthermore, infection with the adenoviral vectors did not adversely affect the integrity of the injured or surrounding tissues. Moreover, no additional reagents, such as matrices or scaffolds, were necessary to achieve the desired healing. In fact, the addition of a collagen matrix together with an adenoviral vector resulted in poor release of the vector to the site of the defect.

What is claimed is:

1. A method of delivering a transgene encoding a factor to a mammalian target cell in a subject wherein administering the factor results in bone formation and/or repair of bone morphologies or reduction of bone degeneration comprising locally administering a delivery vehicle comprising the transgene to a cell in said subject wherein said cell is at the site of a bone pathology and wherein said delivery vehicle is administered in the absence of a bone-compatible matrix, wherein the factor is selected from the group consisting of a growth factor, a cytokine, a growth factor inhibitor and a cytokine inhibitor, wherein the bone pathology to be treated is that selected from the group consisting of healing of a ligamentous transplant, healing of an osseous transplant and healing of a tendinous transplant.

2. The method of claim 1, wherein the delivery vehicle is selected from the group consisting of a viral vector and a non-viral vector.

3. The method of claim 2, wherein said viral vector is selected from the group consisting of an adenoviral vector, an adeno-associated viral vector, and a retroviral vector.

4. The method of claim 2, wherein said nonviral vector is selected from the group consisting of a liposomal vector and a plasmid.

5. The method of claim 1, wherein the factor is selected from the group consisting of transforming growth factory-β (TGF-β), bone morphogenetic protein (BMP), osteogenic protein-1 (OP-1), insulin-like growth factor (IGF), fibroblast growth factor (FGF), platelet-derived growth factor (PDGF), a tumor necrosis factor (TNF) inhibitor, an interleukin-6 inhibitor, a macrophage colony-stimulating factor (M-CSF) inhibitor, a granulocyte/macrophage colony stimulating factor (GM-CSF) inhibitor, an osteoinductive interleukin, and a hedgehog protein.

6. The method of claim 1, wherein the mammalian target cell is selected from the group consisting of a bone cell, a bone marrow cell, a connective tissue cell and a muscle cell.

7. The method of claim 1, wherein said delivery vehicle is administered by an intraosseous route.

8. The method of claim 1, wherein the delivery vehicle is administered to the subject one time.

9. The method of claim 1, wherein the delivery vehicle is administered to the subject multiple times.

* * * * *